(12) United States Patent
De Souza et al.

(10) Patent No.: US 11,066,356 B2
(45) Date of Patent: Jul. 20, 2021

(54) DEVICE AND METHOD FOR THE DESALINATION OF WATER BY MEANS OF THERMAL DEIONISATION AND LIQUID-PHASE ION EXTRACTION LIQUID

(71) Applicant: ADIONICS, Paris (FR)

(72) Inventors: Guillaume De Souza, Brunoy (FR); Jacky Pouessel, Vaugrigneuse (FR); Bastien Dautriche, Angers (FR); Melanie Chtchigrovsky, Gif-sur-yvette (FR); Sebastien Meiries, Belgentier (FR)

(73) Assignee: ADIONICS, Thiais (FR)

( * ) Notice: Subject to any disclaimer, the term of this patent is extended or adjusted under 35 U.S.C. 154(b) by 282 days.

(21) Appl. No.: 15/544,444

(22) PCT Filed: Jan. 18, 2016

(86) PCT No.: PCT/FR2016/050086
§ 371 (c)(1),
(2) Date: Jul. 18, 2017

(87) PCT Pub. No.: WO2016/116687
PCT Pub. Date: Jul. 28, 2016

(65) Prior Publication Data
US 2018/0009738 A1   Jan. 11, 2018

(30) Foreign Application Priority Data
Jan. 19, 2015   (FR) ...................................... 1550391

(51) Int. Cl.
*C07C 233/15*   (2006.01)
*C02F 1/26*   (2006.01)
(Continued)

(52) U.S. Cl.
CPC ........ *C07C 233/15* (2013.01); *B01D 11/0426* (2013.01); *B01D 11/0488* (2013.01);
(Continued)

(58) Field of Classification Search
None
See application file for complete search history.

(56) References Cited

U.S. PATENT DOCUMENTS 3,331,874 A   7/1967   Stecker
3,407,056 A   10/1968   Herbert
(Continued)

FOREIGN PATENT DOCUMENTS

CH   609 558 A5   3/1979
GB   1436306 A   5/1976
(Continued)

OTHER PUBLICATIONS

Levitskaia et al. "Synergistic pseudo-hydroxide extraction: synergism and anion selectivity in sodium extraction using a crown ether and a series of weak lipophilic acids" Anal. Chem. 2003, 75, 405-412 (Year: 2003).*
(Continued)

*Primary Examiner* — Ryan B Huang
(74) *Attorney, Agent, or Firm* — Nixon & Vanderhye

(57) ABSTRACT

Disclosed is a method for treating water, including the extraction of at least two ionic species, the ionic species including an anionic species and a cationic species and being present in the water to be treated, the method especially including a step of mixing a liquid hydrophobic organic phase and the water to be treated, the water to be treated being in the liquid state, in order to subsequently obtain liquid treated water and a hydrophobic liquid organic phase loaded with the ionic species, and a step of thermal regeneration of the organic phase loaded with chemical species.
(Continued)

Also disclosed are compounds and compositions that can be used in the method.

16 Claims, 7 Drawing Sheets

(51) Int. Cl.
| | |
|---|---|
| *B01D 11/04* | (2006.01) |
| *C02F 1/68* | (2006.01) |
| *C02F 103/08* | (2006.01) |
| *C02F 1/38* | (2006.01) |
| *C02F 1/10* | (2006.01) |

(52) U.S. Cl.
CPC .......... B01D 11/0492 (2013.01); C02F 1/265 (2013.01); C02F 1/683 (2013.01); *C02F 1/10* (2013.01); *C02F 1/38* (2013.01); *C02F 2103/08* (2013.01); *C02F 2209/02* (2013.01); *C02F 2303/16* (2013.01); *Y02A 20/124* (2018.01)

(56) References Cited

U.S. PATENT DOCUMENTS

| | | | | |
|---|---|---|---|---|
| 3,408,290 | A * | 10/1968 | Scheibel | B01D 11/0488 210/642 |
| 3,649,219 | A * | 3/1972 | Lynn | B01D 11/0492 423/157 |
| 4,275,234 | A | 6/1981 | Baniel et al. | |
| 6,322,702 | B1 | 11/2001 | Moyer et al. | |
| 6,566,561 | B1 | 5/2003 | Bonnesen et al. | |
| 2008/0014133 | A1 | 1/2008 | Glagolenko et al. | |
| 2008/0179568 | A1 | 7/2008 | Meikrantz et al. | |
| 2010/0176061 | A1* | 7/2010 | Monzyk | C02F 1/56 210/702 |
| 2013/0082003 | A1* | 4/2013 | Bajpayee | C02F 1/26 210/695 |

FOREIGN PATENT DOCUMENTS

| | | |
|---|---|---|
| JP | 558-034005 A | 2/1983 |
| JP | 2010-274252 A | 12/2010 |
| JP | 2015-192979 A | 11/2015 |
| WO | 2010/086575 A1 | 8/2010 |

OTHER PUBLICATIONS

Levitskaia et al. "Synergistic Pseudo-Hydroxide Extraction: Synergism and Anion Selectivity in Sodium Extraction Using a Crown Ether and a Series of Weak Lipophilic Acids". Anal. Chem. 2003, 75, p. 405-412 (Year: 2003).*

EMIS ("Steam stripping". Date accessed Jul. 20, 2020; published Feb. 2010; <URL: https://emis.vito.be/en/bat/tools-overview/sheets/steam-stripping>). (Year: 2010).*

Makrlik et al., "Solvent Extraction of Some Divalent Metal Cations into Nitrobenzene by Using a Synergistic Mixture of Strontium Dicarbollylcobaltate and p-tert-Butylcalix[4]arene-tetrakis (N,N-Diethylacetamide)," Acta Chim. Slov. 2012, 59, pp. 934-938.

Levitskaia et al., "Synergistic Pseudo-Hydroxide Extraction: Synergism and Anion Selectivity in Sodium Extraction Using a Crown Ether and a Series of Weak Lipophilic Acids", Analytical Chemistry, Feb. 1, 2003 (Feb. 1, 2003), pp. 405-412, vol. 75, No. 3.

Popov et al., "Guidelines for NMR measurements for determination of high and low pKa values", Pure and Applied Chemistry, 2006, pp. 663-675, vol. 78. No. 3.

International Search Report and Written Opinion, dated Jun. 13, 2016, from corresponding PCT application No. PCT/FR2016/050086.

FR Search Report and Written Opinion, dated Sep. 7, 2015, from corresponding FR application No. 1550391.

Office Action issued in Indian Patent Application No. 201717028926 dated Oct. 15, 2019 with English translation provided.

Hiraoka, Crown Ether, Biophysics, 1977, vol. 17, No. 3, pp. 36-45.

Saito, Crown Ether, Chemistry Education, 1982, vol. 30, No. 1, pp. 26-30.

* cited by examiner

FIGURE 6

DEVICE AND METHOD FOR THE DESALINATION OF WATER BY MEANS OF THERMAL DEIONISATION AND LIQUID-PHASE ION EXTRACTION LIQUID

TECHNICAL FIELD OF THE INVENTION

The technical field of the invention is ionic extraction applied to the desalination of water, including sea water.

PRIOR ART

A common approach to seawater desalination involves the extraction of water from salt water. It includes water evaporation/condensation technologies by natural or forced heating, at ambient pressure or vacuum and the use of semi permeable membranes (Nanofiltration, reverse osmosis . . . ). Whatever the technology, this approach combines the following disadvantages and shortcomings:

1. A limited level of water valorization because, in excess of 53% of water extraction from a common seawater, there is scaling of the equipments by precipitation of $CaCO_3$, then of $CaSO_4$, or even of $Mg(OH)_2$ and other salts of low relative solubilities contained in the residual water. If the technology employed is associated with a thermal vaporization of this water, the used temperature, generally exceeding 80° C., is then a factor of reduction of the precipitation threshold of certain salts (for example $CaCO_3$ by evaporation of carbon dioxide) and of salts with inverted solubility ($CaSO_4$ in water), generating further reduction of the maximum level of extraction of water from salt water to then only reach 30-35%.

2. An energy-consuming operating mode. Since water is greatly predominant (in wt. % and in mol %) relative to the dissolved ions, extracting the water from the salt water equals to displacing a large quantity of material which is thermodynamically not favorable at all. Thus, vaporization of water is extremely energy-consuming (its latent heat of vaporization is 2319 kJ/kg at 75° C. This is equivalent to burning 74.6 mL of gasoline per liter of vaporized water when standard seawater contains only 36 g of salts per kg of seawater. Thus, in order to reduce the thermal energy consumed, multiple effects or multi-stage flash technologies have been developed employing tanks under vacuum to reduce the thermal energy consumed by an order of magnitude and thus come down to 230 kJ/kg with 12 effects associated with a surplus of investment. Similarly, for membrane permeation or reverse osmosis (representing more than 90 of installed new capacity in 2011) the electrical energy consumed is between 3.5 and 4.5 kWh/m³ of desalinated seawater.

3. The use of stainless steels, which is necessary because of operating pressures which are either much lower than atmospheric pressure (vacuum) or much higher (up to 80 bar) combined to high concentration of chlorides. These products are expensive, but are still not corrosion proof and though can release metallic components from its surface, causing water pollution by toxic metals such as chromium, nickel, molybdenum, manganese and copper.

Another approach to water desalination is to extract the salt out of the salt water. This approach is used in the desalination of low-salinity water (<3-5 g/L) using electro-dialysis membranes, or to obtain ultra-pure water from potable water by using ion exchange resins. This approach is also being developed for a more recent technology, under development, based on capacitive deionization principles (CDI or CapDI), only applicable today to the desalination of low salinity waters, called brackish water. The technological and economic limitation of these systems is essentially due to the transfer and/or storage of ions at membranes, resins or electrodes level. A very high storage area combined with long cycle times do not allow these capacitive deionization technologies to be deployed in seawater treatment today and are therefore limited to low salinities.

Liquid-liquid extraction processes, also known as solvent extraction processes, are nowadays used commercially as a separation technique in chemical engineering. For the separation of ionic compounds, it is now common to separate acidic or basic organic compounds or to purify metals (Zn, Ni, Cu, Co, Cr, Mn . . . ) after their dissolution (leaching) in water (Hydrometallurgy). This separation technique is also used to obtain high purity products such as salts of uranium, plutonium, cesium, strontium or rare earth salts via a liquid-liquid cation exchange process.

A very abundant bibliography exists in this field in which one can quote the article of T. G. Levitskaia, -et al. Anal. Chem. 2003, 75, 405-412 which demonstrates that it is possible to extract sodium hydroxide (NaOH) from an aqueous solution by using a crown ether-like sodium extractant with a lipophilic de-protonable weak acid to allow the formation of a hydrophobic sodium alkoxide.

This document also provides examples of extraction of NaF, NaCl, NaBr, $NaNO_3$ and $NaClO_4$, at 1 M salinity, by combining DC18C6 at 0.02 M without, and then with seven weak acids (from the alcohol family), present at a level of 0.04M, all dissolved in nitrobenzene. Two of these alcohols are fluorinated aromatic alcohols whose pKa is about 8.8. The extraction rate for hydrophobic ions such as the picrate ions is relatively high. However, for hydrophilic anions, such as the chloride ion Cr, the recomputed extraction rates are between 0.06% and 0.16%, which confirms the great difficulty of extracting hydrophilic NaCl from water and the little influence of the alcohols, at this concentration, on the extraction performance.

It has already been proposed in patent application WO 2010/086575, the use in a direct contact exchanger, comprising a liquid and hydrophobic fluorinated phase associated with ion exchangers, such as fluorinated ion exchangers. However, the fluorinated organic liquid phase described in this application depicts the use of ionic organo-fluorinated compounds which are poorly suited to achieving high water desalination rates, for example more than 50%, preferably more than 70%, for hydrophilic alkali salts such as 0.2M NaCl at 25° C. with low operating cost and low energy demand.

The object of the invention is to overcome these disadvantages by providing a new generation of hydrophobic liquid phases having an ion absorption capacity sufficiently temperature-dependent, to allow extraction at low temperature (for example at room temperature) and hot de-extraction, these two steps having a differential temperature, $\Delta T$, greater than 30° C., preferably of 50° C. Other aspects of the invention relate to methods and devices for treating water which make it possible to purify water with a low energy balance.

DESCRIPTION OF THE INVENTION

Thus, the invention relates in particular to a hydrophobic organic liquid composition comprising, or consisting essentially of, or consisting of, at least one first organic compound, preferably protic and hydrophobic, the pKa of which in water at 25° C. is at least 9, preferably at least 10.5, and is preferably less than the pKa of water at 25° C., or at least less than 15 at 25° C., and at least one second organic and hydrophobic compound having a complexing constant of a cationic species whose log K value in methanol at 25° C. is greater than 2 and less than 11, preferably greater than 3 and less than 9.

The first compound is a compound allowing to solvate an anionic species, which is designated by the acronym ASM (for Anion Solvating Molecule). The second compound is a compound allowing to extract (for example solvate or chelate) a cationic species which is designated by the acronym CEM (for Cation Extracting Molecule). Surprisingly, the combination of ASM and CEM according to the invention allows the extraction (or solvation) of cations and more particularly of hydrophilic anions which are particularly difficult to transfer into an organic phase.

The terms "anionic species" and "cationic species" are respectively equivalent to the terms "anions" and "cations".

The pKa (or acid constant) is defined as pKa=$-\log_{10}$(Ka), where Ka is the acid dissociation constant which is measured in a standard manner for such pKa. The recommended standard measurement method for high, basic pKa is preferably that described by Popov and al, IUPAC—*Guidelines for NMR measurements for determination of high and low pKa Pure Appl. Chem.*, Vol. 78, No. 3, pp. 663-675, 2006.

K is the complexing constant of a CEM and a cation in methanol at 25° C. which is measured according to the standard method of isothermal calorimetric titration.

By the term "hydrophobic" is meant a compound, or a mixture of compounds, whose solubility in water at 25° C. is at least less than 0.1 mol/liter. Preferably, hydrophobic compounds are chosen with a water solubility at 25° C. lower than 0.01 mol/l, preferably lower than 0.0001 mol/l and advantageously lower than $1\times10^{-5}$ mol/l. The hydrophobicity or solubility of a compound can be measured by standard methods and in particular by UV-visible spectrometry.

The pKa of the first compound is preferably greater than 9, preferably greater than 10.5, preferably greater than 12, preferably greater than 13 and less than 15.

Alternatively, the pKa of the first compound is chosen in a range from 12 to 15, preferably from 13 to 14. By pKa range from 12 to 15 is meant pKa of 12.1; 12.2; 12.3; 12.4; 12.5; 12.6; 12.7; 12.8; 12.9; 13.0; 13.1; 13.2; 13.3; 13.4; 13.5; 13.6; 13.7; 13.8; 13.9; 14.0; 14.1; 14.2; 14.3; 14.4; 14.5; 14.6; 14.7; 14.8; 14.9 or 15.0.

According to a preferred aspect, the second compound, allowing the extraction, in the composition, of at least one cation, has a complexing constant Log K for said cation ranging from 4 to 8, preferably from 5 to 7. By Log K ranging from 5 to 7 is understood to mean 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9 or 7.0.

Advantageously, this second compound also has a complexing constant for sodium, in water at 25° C., greater than or equal to 1.

The invention also relates to a composition comprising at least one ASM, at least one CEM and, optionally, a fluidifying agent. The compounds ASM and CEM are as described above and/or below.

ASM Compound

An ASM compound as described herein, mixtures and uses thereof in a method of extracting at least one anionic species from water containing said species are also part of the invention.

The ASM can be a compound comprising from 6 to 50 carbon atoms, preferably from 7 to 30 carbon atoms, and in particular from 8 to 20 carbon atoms, and incorporating at least one aromatic ring and at least one halogen atom or an electron-withdrawing group, in particular fluorinated.

Advantageously, the ASM is a compound of formula B:

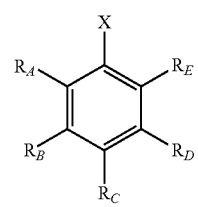

(B)

in which at least one of the radicals $R_A$, $R_B$, $R_C$, $R_D$ and $R_E$, which are identical or different, is an halogen atom or an electron-withdrawing group, in particular an halogenated radical, of the following group:

F, Cl, Br, $CmF_{2m+1}$ with m 4, where m is a non-zero integer, $CF_2CF_2C_pH_{2p+1}$ with p 4, where p is an integer, $CF_2C_pH_{2p+1}$ with p 4, where p is an integer, $CH_2C_pF_{2p+1}$ with p 4, where p is an integer, $OCH_2CF_3$, $C(=O)CF_3$, $C_mH_nF_pCl_qBr_s$ with m≤4, where n, p, q, s are integers of which at least p, q or s is non-zero, $C(=O)OC_mH_{2m+1}$ with m≤4, where m is an integer, and $C(=O)C_mH_{2m+1}$ with m≤4, where m is an integer, the remaining radical(s) $R_A$, $R_B$, $R_C$, $R_D$ and $R_E$ are chosen, identical or different, from the following non-electron withdrawing radicals:

H, $CH_3$, $CH_2CH_3$, $CH_2CH_2C_pF_{2p+1}$ with p≤4, where p is an integer, $C_mH_{2m-1}$ with m≤10, where m is a non-zero integer, and $C_mH_{2m-1}$ with m≤10, where m is a non-zero integer;

where only one of the radicals $R_A$ to $R_E$ may be one of these last two radicals $C_mH_{2m-1}$ and $C_mH_{2m+1}$;

and wherein X is selected from the following radicals:

OH,

NH—R',

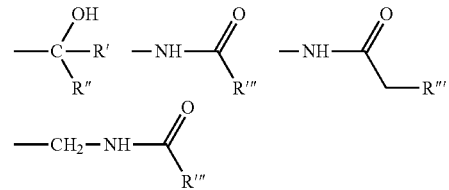

where R' and R", which may be identical or different, are chosen from the following radicals:

H, $C_nH_{2n-1}$ with n≤4, where n is a non-zero integer, $C_nH_{2n+1}$ with n≤4, where n is a non-zero integer, $CH_2CH_2C_pF_{2p+1}$ with p≤4, where p is an integer, $CH_2C_pF_{2p+1}$ with $p \leq 4$, where p is an integer,
$CF_2C_pH_{2p+1}$ with $p \leq 4$, where p is an integer,
$CF_2CF_2C_pH_{2p+1}$ with $p \leq 4$, where p is an integer,
$C_mF_{2m+1}$ with $m \leq 4$, where m is a non-zero integer,
$C_mH_nF_pCl_qBr_s$ with $m \leq 4$, where n, p, q, s are integers of which at least p, q or s is non-zero,
and an aryl radical of formula b:

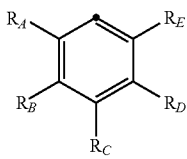

(b)

where $R_A$, $R_B$, $R_C$, $R_D$ and $R_E$, which may be identical or different, are as defined above in formula B;
and wherein R''' is selected from the following radicals:
$C_mH_{2m+1}$ with $m \leq 20$, preferably $\leq 15$, where m is an integer,
$C_mH_{2m+1}$ with $m \leq 20$, where m is a non-zero integer,
$C_mH_nF_pCl_qBr_s$ with $m \leq 10$, where n, p, q, s are integers of which at least p, q or s is non-zero,
$CH_2CH_2C_pF_{2p+1}$ with $p \leq 4$, where p is an integer,
$CH_2C_pF_{2p+1}$ with $p \leq 4$, where p is an integer,
$CF_2C_pH_{2p+1}$ with $p \leq 4$, where m is an integer,
$CF_2CF_2C_pH_{2p+1}$ with $p \leq 4$, where m is an integer,
$C_mF_{2m+1}$ with $m \leq 4$, where m is a non-zero integer,
and an aryl radical of formula b:

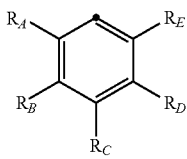

(b)

where $R_A$, $R_B$, $R_C$, $R_D$ and $R_E$, which may be identical or different, are as defined above in formula B.

ASM Compound—Alcohol

Such a compound is advantageously chosen from the group of fluorinated aromatic alcohols. For example, this compound may be a phenol derivative, such as 3-(trifluoromethyl)phenol (CAS No. 98-17-9).

Preferably, this first compound is a methanolic phenyl compound which advantageously comprises more than 3 fluorine atoms. Advantageously, this compound comprises more than two —$CF_3$ radicals.

According to one embodiment of the invention, this first compound is a compound of formula A:

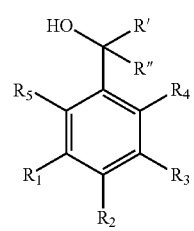

(A)

in which
$R_1$, $R_2$, $R_3$, $R_4$ and $R_5$, which may be identical or different, but where any one of $R_1$, $R_2$ and $R_3$ is a fluorinated radical, are chosen from the following radicals:
H,
F,
$C_mF_{2m+1}$ with $m \leq 4$, where m is a non-zero integer,
$CF_2C_pH_{2p+1}$ with $p \leq 4$, where p is a non-zero integer, and
$CF_2CF_2C_pH_{2p+1}$ with $p \leq 4$, where p is a non-zero integer;
and in which R' and R'', which may be identical or different, are chosen from the following radicals:
H
$C_nH_{2n-1}$ with $n \leq 4$, where n is a non-zero integer,
$C_nH_{2n+1}$ with $n \leq 4$, where n is a non-zero integer,
$CH_2C_pF_{2p+1}$ where $p \leq 2$, where p is a non-zero integer,
$CH_2CH_2C_pF_{2p+1}$ where $p \leq 2$, where p is a non-zero integer,
and an aryl radical of formula a:

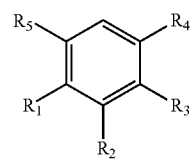

(a)

wherein $R_1$, $R_2$, $R_3$, $R_4$ and $R_5$, which may be identical or different, are selected from the group
H,
F,
$C_mF_{2m+1}$ with $m \leq 4$,
$CF_2C_pH_{2p+1}$ with $p \leq 4$, where p is a non-zero integer,
$CF_2CF_2C_pH_{2p+1}$ with $p \leq 4$, where p is a non-zero integer.

Advantageously, said first compound is selected from the group consisting of the compounds described in Table I below:

TABLE I

| ASM Semi-developed formula | Molecular formula CAS n° | Molar Weight (g/mole) | Density (g/cm3) | [ASM] maximum Mole/L | Solubility in water mMole/L | pKa |
|---|---|---|---|---|---|---|
| HO—⌬—CF_3 | $C_8H_7F_3O$ 349-75-7 | 176.14 | 1.29 Liquid | 7.32 | 32 | 14.6 +/− 1.0 (estimated) |

TABLE I-continued
| ASM Semi-developed formula | Molecular formula CAS n° | Molar Weight (g/mole) | Density (g/cm3) | [ASM] maximum Mole/L | Solubility in water mMole/L | pKa |
| --- | --- | --- | --- | --- | --- | --- |
| 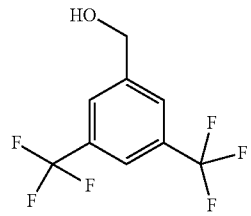 [SMILES: OCc1cc(C(F)(F)F)cc(C(F)(F)F)c1] | $C_9H_6F_6O$ 32707-89-4 | 244.13 | 1.43 Solid | 5.86 | 2.29 | 14.5 +/− 1.0 (estimated) |
| 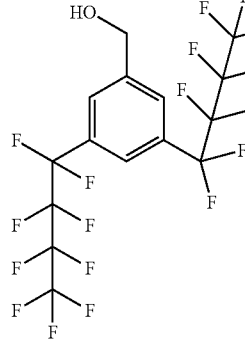 | $C_{15}H_6F_{18}O$ 916975-23-0 | 544.18 | 1.62 | 2.98 | 0.0005 | 14.01 +/− 0.1 |
| 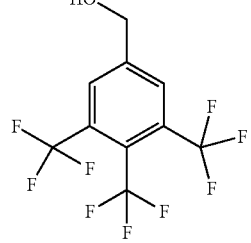 | $C_{10}H_5F_9O$ 1010101-84-4 | 312.13 | 1.53 | 4.90 | 0.39 | 13.59 +/− 0.1 |
| 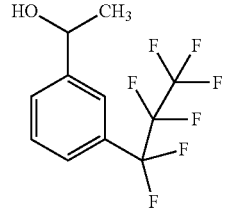 | $C_{11}H_9F_7O$ 131608-30-5 | 290.18 | 1.39 | 4.70 | 0.42 | 14.5 +/− 1.0 (estimated) |
| 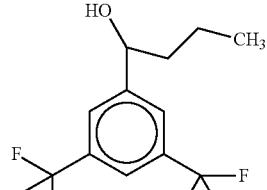 | $C_{12}H_{12}F_6O$ 742097-71-8 | 286.21 | 1.30 Liquid | 4.54 | 0.48 | 13.9 +/− 1.0 (estimated) |
| 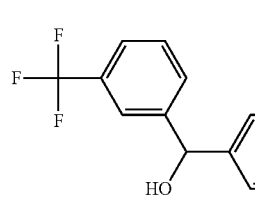 | $C_{15}H_{10}F_6O$ 1598-89-6 | 320.23 | 1.37 Liquid | 4.28 | 0.07 | 13.3 +/− 1.0 (estimated) | and the compounds ASM 2, ASM 3 and ASM 5 described hereinafter.

According to one aspect of the invention, the hydrophobic organic liquid composition comprises at least two compounds allowing the solvation of at least one anion. Preferably, these compounds are chosen from the (ASM) type compounds described in the present application.

In particular, the liquid composition according to the invention may comprise a mixture of [3-(Trifluoromethyl) phenyl]methanol (CAS No. 349-75-7) and of [3,5-Bis(Trifluoromethyl)phenyl]methanol (CAS No: 32707-89-4). The relative volume ratio of these compounds relative to each other may vary, but is advantageously in a ratio ranging from 30/70 to 50/50 volume/volume (v/v). Preferably this ratio is about 40/60 v/v.

Alternatively, the liquid composition according to the invention may comprise a mixture of 3-(Perfluorobutyl) phenyl]methanol (ASM 5) and 3,5-(Perfluoropropyl)phenyl]methanol (ASM 6). The relative proportion of these compounds relative to each other may vary, but is advantageously in a ratio ranging from 60/40 to 80/20 v/v. Preferably this ratio is about 70/30 v/v.

ASM—Amide Compound

The ASM compound of formula B may also be an amide compound. In this case, the X radical in formula B, is:

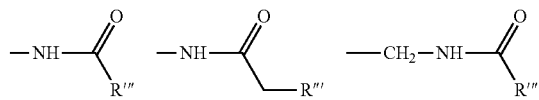

Where R''' is as previously described.
Preferably, the amide has the formula:

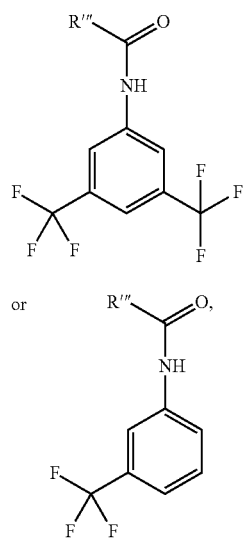

in which R''' is chosen from the following radicals:
  $C_mH_{2m+1}$ with m≤20, preferably ≤15 where m is an integer,
  $C_mH_{2m+1}$ with m≤20, where m is a non-zero integer,
  $C_mH_nF_pCl_qBr_s$ with m≤10, where n, p, q, s are integers of which at least p, q or s is non-zero, and an aryl radical of formula b:

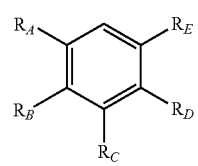

in which at least one of the radicals $R_A$, $R_B$, $R_C$, $R_D$ and $R_E$, which are identical or different, is an halogen atom or an electron-withdrawing group, in particular a halogenated radical, of the following group:
  F, Cl, Br,
  $C_mF_{2m+1}$ with m≤4, where m is a non-zero integer,
  $CF_2CF_2C_pH_{2p+1}$ with p≤4, where p is an integer,
  $CF_2C_pH_{2p+1}$ with p≤4, where p is an integer,
  $CH_2C_pF_{2p+1}$ with p≤4, where p is an integer,
  $OCH_2CF_3$,
  $C(=O)CF_3$,
  $C_mH_nF_pCl_qBr_s$ with m≤4, where n, p, q, s are integers of which at least p, q or s is non-zero,
  $C(=O)OC_mH_{2m+1}$ with m≤4, where m is an integer, and
  $C(=O)C_mH_{2m+1}$ with m≤4, where m is an integer, the remaining radical(s) $R_A$, $R_B$, $R_C$, $R_D$ and $R_E$ are chosen, identical or different, from the following non-electron withdrawing radicals:
  H,
  $CH_3$,
  $CH_2CH_3$,
  $CH_2CH_2C_pF_{2p+1}$ with p≤4, where p is an integer,
  $C_mH_{2m+1}$ with m≤10, where m is a non-zero integer, and
  $C_mH_{2m+1}$ with m≤10, where m is a non-zero integer
where only one of the radicals $R_A$ to $R_E$ may be one of these last two radicals $C_mH_{2m-1}$ and $C_mH_{2m+1}$.

Preferably, the radical R''' is a linear or non-linear alkyl chain, and in particular an n-$C_7H_{15}$, n-$C_9H_{19}$, n-$C_{11}H_{23}$ or n-$C_{13}H_{27}$ radical.

These amide compounds are particularly suitable for the temperature difference extraction method according to the invention. Other compounds of this type which can be used as ASM for extraction compositions according to the invention are, for example:
  the N-[3,5-Bis(trifluoromethyl)phenyl] acetamide (CAS No. 16143-84-3),
  the N-[3,5-Bis(trifluoromethyl)phenyl]-2-chloroacetamide (CAS No. 790-75-0),
  the N-[3,5-Bis(trifluoromethyl)phenyl]-2-bromoacetamide (CAS No. 99468-72-1),
  the N-[3,5-Bis(trifluoromethyl)phenyl]-2-chlorobenzamide (CAS No. 56661-47-3),
  the N-[3,5-Bis(trifluoromethyl)phenyl]-4-chlorobenzamide (CAS No. 56661-30-4),
  the N-[3,5-Bis(trifluoromethyl)phenyl]-4-bromobenzamide (CAS No. 56661-31-5),
  the N-[3,5-dichlorophenyl] acetamide (CAS No. 31592-84-4),
  the N-[4-methyl-3,5-dichlorophenyl] acetamide (CAS No. 39182-94-0),
  the N-[3-fluoro-5-(trifluoromethyl)phenyl] acetamide (CAS No. 402-02-8),
  the N-[2-fluoro-5-(trifluoromethyl)phenyl] acetamide (CAS No. 349-27-9),
  the N-[4-chloro-3-(trifluoromethyl)phenyl] acetamide (CAS No. 348-90-3), the N-[4-bromo-3-(trifluoromethyl)phenyl] acetamide (CAS No. 41513-05-7),
the N-[2,5-difluoro-3-(trifluoromethyl)phenyl] acetamide (CAS No. 1994-23-6),
the N-[3-(trifluoromethyl)phenyl] acetamide (CAS No. 351-36-0),
the N-[2-methyl-3-(trifluoromethyl)phenyl] acetamide (CAS No. 546434-38-2),
the N-[2-amino-3-(trifluoromethyl)phenyl] acetamide (CAS No. 1579-89-1),
the N-[3-(trifluoromethyl)phenyl]-2,2,2-trifluoroacetamide (CAS No. 2946-73-8),
the N-[3-(trifluoromethyl)phenyl]-2,2-dichloroacetamide (CAS No. 2837-61-8),
the N-[3-(trifluoromethyl)phenyl]-2,2,2-trichloroacetamide (CAS No. 1939-29-3),
the N-[4-chloro-3-(trifluoromethyl)phenyl]-2,2,2-trichloroacetamide (CAS No. 13692-04-1),
the N-[3-(trifluoromethyl)phenyl]-2-bromoacetamide (CAS No. 25625-57-4),
the N-[3-(trifluoromethyl)phenyl]propanamide (CAS No. 2300-88-1),
the N-[2-chloro-5-(trifluoromethyl)phenyl]propanamide (CAS No. 721-57-3),
the N-[3-(trifluoromethyl)phenyl](2,2-dimethyl-propanamide) (CAS No. 1939-19-1),
the N-[2-methyl-3-(trifluoromethyl)phenyl](2,2-dimethyl-propanamide) (CAS No. 150783-50-9),
the N-[4-chloro-2-methyl-3-(trifluoromethyl)phenyl](2,2-dimethyl-propanamide) (No. CAS 112641-23-3),
the N-[3-(trifluoromethyl)phenyl](2-chloro-propanamide) (No. CAS 36040-85-4),
the N-[3-(trifluoromethyl)phenyl]butanamide (No. CAS 2339-19-7),
the N-[3-(trifluoromethyl) phenyl]isobutanamide (No. CAS 1939-27-1),
the N-[3-(Trifluoromethyl)phenyl]cyclopentanecarboxamide.(No. CAS 13691-84-4),
the N-[3-(trifluoromethyl)phenyl](2-methyl-pentanamide) (No CAS 1939-26-0),
the N-[3-(trifluoromethyl)phenyl](2,2-Dimethyl-pentanamide) (No CAS 2300-87-0),
the N-[3-(trifluoromethyl)phenyl](2-(4-Bromophenyl)-acetamide) (No CAS 349420-02-6),
the N-[3-(Trifluoromethyl)phenyl]-1-adamantanecarboxamide (No CAS 42600-84-0),
the N-[2-chloro-5-(trifluoromethyl)phenyl]octanamide (No CAS 4456-59-1).

These molecules, used as ASM, by their integration in a formulation combining at least one CEM and optionally a fluidifying agent, make it possible to extract ionic species and in particular hydrophilic salts from water to the organic extractant phase. Another object of the invention relates to the use of these ASM compounds and in particular ASM amides for desalting salt water and/or for extracting salts and/or ions from an aqueous medium. In particular, these compounds can be used, individually or as a mixture, in a composition or a method according to the invention as described in the present application.

ASM Concentration in the Organic Liquid Composition

According to a preferred aspect of the invention, the molar concentration of the first ASM compound (or of a mixture of such compounds) in the composition according to the invention is at least equal to 0.1 M. Preferably this composition is higher, and is at least equal to 1 M so as to allow an optimized extraction, in particular of the hydrophilic anions. It may also be at least equal to 2 M, advantageously at least equal to 3 M, for example at least equal to 4 M. In certain variants of the invention, the first compound or a mixture of first compounds may be used pure (molar concentration of 7.32 M for CAS No. 349-75-7).

Density and Solubility and Viscosity

According to an advantageous aspect of the invention, the first compound allowing the solvation in the composition of at least one anion, has a solubility in water, in its free or complexed form, of less than 0.1 Mol/L, preferably less than 0.01 Mol/L, preferably less than 0.0001 Mol/L and more particularly less than $1\times10^{-5}$ Mol/L.

According to another advantageous aspect of the invention, the first compound allowing the solvation, in the composition, of at least one anion has a density greater than 1.1 kg/L, ideally greater than 1.2 kg/liter.

According to yet another advantageous aspect of the invention, the first compound allowing the solvation, in the composition, of at least one anion has a viscosity at 25° C. of less than 100 mPa·s, preferably less than 50 mPa·s, for example less than 20 mPa·s.

CEM

The second compound, which makes it possible to extract at least one cation (CEM), may advantageously be chosen from molecules having good alkaline ion extraction capacity, such as, for example, sodium ions and/or alkaline-earth ions or other cations depending on the separation need. The extraction may be due to a replacement of the solvation of the cations and anions with water by solvating them with the extracting composition which then allows interaction with the CEM and the ASM. The nature of the interactions covers phenomena such as ion-dipole interactions, accompanied by the establishment of hydrogen bonds and electrostatic interactions, and even van der Waals bonds. Preferably, the CEM is a compound for complexing, and in particular chelating the cation. The "chelate" is distinguished from the simple "complex" by the fact that the cation is attached to the chelating ligand by at least two bonds/interactions.

The second compound may advantageously be chosen from the group of nonionic (or neutral) and/or non-fluorinated compounds. The use of a crown ether having a carbon number ranging from 14 to 80, especially non fluorinated crown ethers, may be considered.

The term "crown ether" is intended to mean a cyclic molecule having a carbon number ranging from 14 to 80, the crown ether having 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48,49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 carbon atoms.

Thus the second compound may be selected from the group consisting of DB21C7, B15C5, C15C5, DC18C6, DB18C6, DB24C8, Calix[4]Est, and a substituted calixarene other than Calix[4]Est. The formula of these compounds being indicated below.

The second compound is preferably a substituted calixarene which may comprise, for example, from 32 to 80 carbon atoms, and more particularly from 50 to 70 atoms, for example from 58 to 60 carbon atoms. The 4-tert-butylcalix[4] arene-O,O',O''',O'''-tetraacetic Acid Tetraethyl Ester is particularly preferred for the extraction of sodium.

The composition according to the invention may also comprise more than one compound allowing the extraction of at least one cation, which can advantageously be chosen from the compounds described in the present application.

Density and Solubility and Viscosity

According to a preferred aspect of the invention, the second compound allowing the extraction, in the composition, of at least one cation has a solubility in water, in its free form or complexed to the cation, of less than 0.1 Mol/L, preferably less than 0.01 Mol/L, preferably less than 0.0001 Mol/L and more particularly less than $1\times10^{-5}$ Mol/L.

According to another preferred aspect of the invention, the second compound allowing the extraction, in the composition, of at least one cation has a solubility in the first compound (ASM) at 25° C. greater than 0.2 M/L, preferably greater than 0.5 M/L, for example greater than 1 M/L.

According to another preferred aspect of the invention, the second compound allowing the extraction, in the composition, of at least one cation has a density greater than 0.8 kg/L, preferably greater than 1.0 kg/L, ideally greater than 1.2 kg/L.

According to another preferred aspect of the invention, the second compound allowing the extraction in the liquid of at least one cation is a liquid and has a viscosity at 25° C. of less than 100 mPa·s, preferably less than 50 mPa·s, for example less than 20 mPa·s.

Relative concentration of ASM and CEM in the organic liquid composition

To ensure maximum extraction of the ionic species, the concentrations of ASM and CEM are chosen as a function of the concentration in the aqueous solution of the ionic species to be extracted.

Thus, at iso-volume of salt water and extraction formulation, the concentration of the CEM compound is advantageously equimolar or higher than the concentration of the cation to be extracted. A concentration about twice as high generally constitutes a limit beyond which cation extraction is not substantially improved.

Surprisingly, a molar concentration of ASM much higher than that of the anion to be extracted may be required to allow an optimized extraction. Thus, at least twice, preferably four times, more than fivefold or sixfold, or more, of the concentration of the anion to be extracted may be necessary to obtain satisfactory results, particularly when the anion is the chloride anion.

Thus, the relative molar ratio of ASM/CEM of a composition according to the invention for extracting a salt consisting of an anion and a cation is advantageously greater than or equal to 1, 2, 3, 4, 5 or 6. The choice of the relative molar proportion ASM/CEM to be used for an industrial application is dependent on the relative cost of these compounds and on the technical and economic data of the project. Preferably, this proportion is at least equal to 4 for an Alcohol ASM and between 1 and 4 for an Amide ASM.

Use of the Composition According to the Invention

The composition according to the invention can advantageously be used to extract hydrophilic ions (cations, anions) from an aqueous phase. It should be noted that this ion extraction is not compensated by the transfer of chemical, ionic or other species, from the organic phase to the aqueous phase. This composition is particularly suited to the extraction of ionic species present in salt water and in particular seawater. This composition can advantageously be used for desalination of seawater and generally purification or treatment of salt water. By "salty" is meant a water comprising at least one salt. By "salt" is meant an ionic compound composed of cations and anions forming a neutral product and without net charge. These ions can be both inorganic (chloride $Cl^-$, $Na^+$ ion . . . ), as well as organic (acetate $CH_3$–$COO^-$, ammonium $R_3NH^+$ . . . ) and monoatomic (fluoride $F^-$, $Mg^{2+}$ ion . . . ) as well as polyatomic (nitrates $NO_3^-$, Hydrogen carbonate $HCO_3^-$, sulfate $SO_4^{2-}$, etc.).

The composition according to the invention is therefore particularly suitable for use in an ion extraction method or device according to any of the other objects of the invention described in the present application.

Anions and Cations to be Extracted

The first and second compounds included in the composition according to the invention are compounds allowing the solvation and extraction of at least one, and preferably several, ionic species constituting alkali or alkaline earth metal salts. In particular, these ionic species are those present in sea water and are listed, as well as their respective concentrations, in Table II.

TABLE II

| Sea Water | Mol/m$^3$ | g/m$^3$-mg/L |
|---|---|---|
| Br$^-$ | 0.8 | 67.7 |
| Cl$^-$ | 545.8 | 19,349.8 |
| HCO$_3^-$ | 1.8 | 108.2 |
| F$^-$ | 0.1 | 1.4 |
| CO$_3^{--}$ | 0.3 | 15.8 |
| SO$_4^{--}$ | 28.2 | 2,711.0 |
| Mg$^{++}$ | 52.4 | 1,273.7 |
| Ca$^{++}$ | 10.3 | 412.0 |
| Sr$^{++}$ | 0.09 | 7.7 |
| Na$^+$ | 469.3 | 10,793.1 |
| K$^+$ | 10.7 | 417.5 |
| | 1,120 | 35,158 |

Accordingly, the compositions according to the invention can be used in methods according to the invention for extracting $Na^+$ or $K^+$ or a mixture of $Na^+$ and $K^+$ in an organic phase. Preferably, the anion solvated by the composition according to the invention is a hydrophilic anion, such as, for example, $Cl^-$ or $SO_4^{2-}$ or $HCO_3^-$ or a mixture of $Cl^-$ and $SO_4^{2-}$. Thus, the composition according to the invention is particularly suitable for the extraction of an aqueous phase of NaCl, Na$_2$SO$_4$, NaHCO$_3$, KCl, K$_2$SO$_4$ or KHCO$_3$, or the extraction of a mixture of NaCl and Na$_2$SO$_4$, NaCl and NaHCO$_3$, NaCl and KCl, NaCl and K$_2$SO$_4$ or NaCl and KHCO$_3$, or any one of these salt mixtures, or a mixture of NaCl and Na$_2$SO$_4$ and NaHCO$_3$ and KCl and K$_2$SO$_4$ and KHCO$_3$.

Alternatively, or additionally, the anions extracted are fluorides, bromides, $HCO_3^-$, nitrates $NO_3^-$, $CN^-$, $OH^-$, nitrites $NO_2^-$, carbonates $CO_3^{2-}$, or $ClO_2^-$ or sulfite $SO_3^{2-}$ or others.

For the more hydrophobic anions such as perchlorates $ClO_4^-$, permanganates $MnO_4^-$, picrates, lower concentrations of ASM are sufficient to allow their transfer to the organic phase in combination with at least one cation complexed by an ECM.

Fluidifying Agent

Some of the CEMs and ASMs being solid or viscous compounds at the operating temperatures of the extraction method, then the use of a fluidifying agent is advantageous. Since the method according to the invention makes it possible in particular to extract relatively high concentrations of salts, it is necessary to identify a solubilizer capable of dissolving at least 0.1 mol/L of combined CEM and ASM. Indeed, conventional solvents such as acetone, ethyl acetate, heptane, dimethylformamide, nitromethane, methanol, ethanol, diethyl ether or acetonitrile, for example, do not solubilize at these levels of concentration number of known CEMs and in particular the Calix[4]Ester, which is a CEM of interest.

On the other hand, it appears that solvents such as chloroform and more particularly polar aromatic solvents have the capacity to be good candidates as a solubilizer for this application. This can be explained by the similar nature of ASMs, themselves generally aromatic compounds. For example, 1,3-bis(trifluoromethyl)benzene (CAS No. 402-31-3) and more preferably benzyl benzoate (CAS No. 120-51-4) composed of two aromatic rings satisfy this criterion of solubilization on tested formulations incorporating Calix[4]Ester and ASM3. Thus, the presence of at least one trifluoromethyl-electron-withdrawing group on one aromatic ring or on 2 aromatic rings makes it possible to obtain particularly advantageous fluidifying compounds.

According to a preferred aspect of the invention, the composition consists only of the ASM and CEM compounds, and optionally in combination with a fluidifying compound, thus constituting a composition consisting of ASM and CEM and of a fluidifying compound.

According to a preferred aspect of the invention, the composition does not comprise compounds classified as hazardous and does not exhibit a skin irritation effect, is non-allergenic and does not present an acute oral toxicology.

Preferably, the composition according to the invention does not contain nitrobenzene.

Preferably, the composition according to the invention comprises a fluorinated aromatic compound comprising more than 3 fluorine atoms and an CEM having a complexing constant in methanol at 25° C. of between 3 and 9. The CEM may be, for example, an Ether-crown, a Cryptand or a functionalized Calixarene, such as, for example, Cali[4]Ester.

Another object of the invention relates to the compound 3-(Perfluorobutyl)phenyl]methanol.

Yet another object of the invention relates to the compound 3,5-(Perfluoropropyl) phenyl]methanol.

The invention further relates to a composition comprising, consisting essentially of or consisting of a mixture of [3-(Perfluorobutyl)phenyl]methanol and 3,5-(Perfluoropropyl) phenyl]methanol.

These two compounds are novel, as is the composition comprising them.

Another object of the invention is the use of 3-(Perfluorobutyl)phenyl]methanol and/or 3,5-(Perfluoropropyl)phenyl]methanol, alone or as a mixture, for salt water desalination and/or for the extraction of salts and/or ions from an aqueous medium. In particular, these compounds can be used, individually or as a mixture, in a composition or in a method according to the invention as described in the present application.

According to a preferred embodiment, the composition does not comprise an ECM allowing the extraction of calcium ions.

The invention also relates to a method for treating water comprising the extraction of at least two ionic species, said ionic species comprising an anionic species and a cationic species being present in the water to be treated, said method comprising the following steps:

a) mixing in a first reactor, at a first temperature, between an hydrophobic organic liquid phase and the water to be treated, said water to be treated being in the liquid state, in order to subsequently obtain a treated liquid water and an hydrophobic organic liquid phase charged with said ionic species, said hydrophobic phase comprising a first and a second hydrophobic compounds as described in the present application and in particular:

a first organic compound, preferably protic, and hydrophobic whose pKa in water at 25° C. is at least 9, preferably 10.5 and is preferably less than the pKa of water at 25° C., or at least less than 15 to 25° C., and a second hydrophobic organic compound having a complexing constant whose log K value, in methanol at 25° C., is greater than 2 and less than 11, preferably greater than 3 and less than 9;

b) separating, on one hand, of said treated liquid water and on the other hand of said organic liquid phase charged with said ionic species, c) mixing, at a second temperature, in the liquid phase, in a second reactor, of said organic liquid phase, charged with ionic species, with regeneration liquid water, for the subsequent production of a regenerated organic liquid phase and of a regeneration liquid water charged with ionic species, the difference between said first and second temperatures going from 30° C. to 150° C.

Alternatively, the invention also relates to a method as described above but in which the first organic compound is an ASM and the second organic compound is a CEM. According to another variant of the invention, the method is as described above, but the first and second organic compounds are comprised in an extracting composition according to the invention.

In contrast to many known extraction methods, the method according to the invention is not based on a change in pH to allow either the absorption or the release of the captured ions, in particular via an acid-base mobility of the hydrogen ion H. Thus, a preferred aspect of the invention is that the method does not include a step in which the pH of the regeneration liquid water is significantly modified, that is to say, beyond a variation of pH of +/−2, for example ±1 relative to the water to be treated.

Since the method is particularly suitable for desalination of sea water, the ionic species considered may be one of those described in Table II above. Furthermore, this method advantageously makes it possible to extract from the water to be treated, at least one alkaline or alkaline-earth cationic species as well as anionic species such as $Cl^-$ or $SO_4^{2-}$ ions. It should be noted that such anionic species are hydrophilic and particularly difficult to extract from an aqueous medium. A particularly advantageous aspect of the method according to the invention is that it can allow the extraction of an aqueous phase of $Na^+$, $Cl^-$, $SO_4^{2-}$, and $K^+$ simultaneously.

Step a)

The mixing step a) of the water to be treated and of the organic phase can be carried out by stirring the two liquid phases, for example by rotation, centrifugation, and/or by vertical interpenetration (gravitational column) when these two phases are of different densities. The latter aspect is what is preferred. Also, the organic phase is advantageously chosen to have a higher density than the density of the water to be treated and of the treated water. Alternatively, the organic phase may be chosen to have a lower density than the density of the water to be treated and the treated water. In these two cases, the density differential must be sufficient to allow an effective interpenetration of the two phases when this type of mixture is used. In this case, this differential is advantageously at least of 0.1 kg/L. However, if other mixing means are used, such as centrifugation, then this differential may be as low as 0.05 kg/L.

It is also preferred that the step of mixing a) does not take place under conditions that result in a stable microemulsion or emulsion.

Step b)

The step for separating the aqueous and organic phases may advantageously be a simple gravitational decantation of the organic phase and of the liquid aqueous phase. This decantation can take place in the reactor where the mixture is made. Alternatively, the separation may be achieved by the application of an external means, for example centrifugation, optionally in a specific centrifuge unit, away from the reactor where the aqueous and organic phases are mixed.

Step c)

Once the phases are separated, the liquid organic phase charged with ionic species is directed to the second reactor where it is brought into contact with liquid water, or regeneration water. With the exception of temperature, this mixing step c) can be carried out under similar operating conditions to those described for the mixing step a). However, some of the conditions, such as, for example, the pressure, may vary to avoid, for example, boiling of the water or of the fluidifying agent.

Temperature

According to a particularly advantageous aspect of the invention, step a) is carried out at ambient temperature. It is also advantageous for the water to be treated, not to be subjected to a preliminary heating or cooling step. Alternatively, a preheating or cooling step may take place. In this case, it is preferable that the water to be treated is not heated or cooled by more than 5° C., advantageously by more than 2° C., when compared to the unheated or uncooled water to be treated.

According to another advantageous aspect of the invention, the first temperature is at a temperature of less than 50° C. but advantageously greater than 0° C. This temperature can be chosen in ranges from 10° C. to 40° C., preferably from 15° C. to 30° C., and particularly preferably from 19 to 26° C. (for example, 25° C.).

By temperature range from 10° C. to 50° C. is meant temperatures of 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C.

According to another advantageous aspect of the invention, the second temperature is a temperature higher than 50° C., preferably higher than 70° C. This temperature can be chosen in the range from 50° C. to 150° C., preferably from 70° C. to 110° C., particularly preferably from 80° C. to 90° C. (for example, 85° C.).

By temperature range from 50° C. to 150° C. is meant temperatures of 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 122° C., 124° C., 126° C., 128° C., 130° C., 132° C., 134° C., 136° C., 138° C., 140° C., 142° C., 144° C., 146° C., 148° C. or 150° C.

The first and second temperatures are necessarily chosen so that the mixture remains in the liquid state at the operating pressure. It is particularly advantageous if the difference between these temperatures, $\Delta T$, is chosen within a range from 30° C. to 150° C., preferably from 50° C. to 75° C. By $\Delta T$ ranging from 50° C. to 75° C. is meant a $\Delta T$ of 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C. or 75° C. So, if the first temperature is at 20° C., the second temperature will be above 50° C., advantageously above 70° C.

Thus, the method of the invention may comprise a first step a) allowing the transfer of ionic species from the water to be treated to the organic phase at ambient temperature, followed by a step c) allowing the regeneration of the organic phase which is charged in ionic species and which takes place at a temperature above the ambient temperature but still relatively low (for example below 150° C.).

According to a preferred aspect of the method, it comprises the following steps:

d) separating said regenerated organic liquid phase and regeneration liquid water charged with said ionic species, e) indirect thermal contacting, for example by a heat exchanger, of said organic liquid phase charged with ionic species and of said regenerated organic liquid phase.

According to a particular aspect of the invention, it is advantageous for the method to comprise heating and/or cooling steps of:

the organic phase charged with ionic species,
the organic phase, in particular regenerated, not charged with ionic species,
the water to be treated,
the treated water, and/or
the regeneration water;

which precedes the introduction of these various phases or waters into the first and second reactors.

Such heating steps may be carried out in whole or in part by heat exchanges between at least two of the aforementioned various phases (that is to say the organic phases and the aqueous phases that are the water to be treated, treated water and ionic species charged water (saline water)).

In particular, the method according to the invention comprises a step of heating the regeneration water carried out before step c).

Pressure

The mixing steps a) and/or c) are advantageously carried out at atmospheric pressure of about 1 atm at sea level or without the application of pressure means other than the weight of the liquids present in the reactor.

If pressure is applied, it may be positive or negative. Such a pressure may range from 0.8 atm to 80 atmospheres, preferably from 1 to 10 atm.

Use of Treated Water

Advantageously, the regeneration liquid water used in step c) is a part of the treated water obtained from step a). Alternatively it may come from an external source.

Composition

The organic phase comprises, or consists essentially of, or consists of, the composition according to the invention which is described in the present application. This composition is particularly effective for carrying out said method. Compositions particularly suitable for carrying out the method according to the invention comprise compositions ASM 7 and ASM 4 associated with calixarene compounds such as 4-tert-Butylcalix [4] arene-O,O',O'',O'''-tetraacetic acid tetraethyl ester.

In the description of the invention, this composition can also be called "solvent" or "resin".

Device

The invention also relates to a device for extracting at least two ionic species, said ionic species comprising at least one anionic species and one cationic species present in the water to be treated, comprising:

a first reactor comprising a liquid hydrophobic organic phase or composition according to the invention as described in the present application.

This device may advantageously comprise:

a first reactor comprising the said hydrophobic and liquid organic composition and optionally the water to be treated, said water to be treated being in the liquid state, for the subsequent production of a treated liquid water and an hydrophobic organic liquid phase charged with said ionic species, said first reactor further comprising first mixing means and first means for separating, on the one hand, said treated liquid water and on the other hand said charged organic liquid phase, a second reactor comprising an hydrophobic organic liquid phase charged with ionic species and optionally regeneration treated liquid water coming from said first reactor to subsequently obtain regeneration liquid water charged with said ionic species and a regenerated organic phase, said second reactor comprising second mixing means and second means for separating, on the one hand, said liquid water charged with ionic species and, on the other hand, said regenerated organic phase;

optionally means for controlling the temperature in said second reactor;

connexion means allowing the transfer between the first and the second reactor of:
- said regeneration treated liquid water extracted from said first reactor
- said charged hydrophobic organic liquid phase extracted from said first reactor
- said regenerated hydrophobic organic liquid phase extracted from said second reactor; and eventually,
- a heat exchanger bringing together on the one hand said charged hydrophobic organic liquid phase extracted from said first reactor and on the other hand said regenerated hydrophobic organic liquid phase extracted from said second reactor and/or said liquid water charged with ionic species.

According to a particular aspect of the invention, the reactors, and more particularly those parts of these reactors which are not moving, are not made of stainless steel.

According to another particular aspect of the invention, the first and/or the second reactor does not comprise heating (heaters) or cooling (cooler) means.

According to yet another particular aspect of the invention, the organic phase present in the device comprises, or consists essentially, or consists of, the composition according to the invention described in the present application.

The device according to the invention may advantageously be mounted in series to enable successive treatment steps of the water to be treated in order to reduce the concentration in ionic species of the water until pure and/or potable water is obtained. Such a device is also covered by the present invention.

Other Embodiment

According to another embodiment, the invention relates to a method for treating water comprising the extraction of at least two ionic species made of an anionic species and a cationic species, present in the water to be treated and comprising the following steps:

a) mixing in a first reactor, at a first temperature, between an hydrophobic organic liquid phase and the water to be treated, said water to be treated being in the liquid state, in order to subsequently obtain a treated liquid water and an hydrophobic organic liquid phase charged with the said ionic species, said hydrophobic phase comprising:

a first protic and hydrophobic organic compound allowing anionic species solvation and whose pKa in water at 25° C. is advantageously of at least 11 and lower than that of water at 25° C., or at least lower than 15 at 25° C., and a second hydrophobic organic compound allowing cation extraction and advantageously having a complexing constant of said cationic species whose log K value, in methanol at 25° C., is greater than 2 and less than 11, preferably greater than 3 and less than 9;

b) separating, on one hand, of said treated liquid water and on the other hand of said organic liquid phase charged with said ionic species, c) mixing, at a second temperature, in the liquid phase, in a second reactor, of said organic liquid phase, charged with ionic species, with regeneration liquid water, for the subsequent production of a regenerated organic liquid phase and of a regeneration liquid water charged with ionic species;

said organic phase loaded with ionic species containing little or no calcium ions.

According to a preferred embodiment, the organic phase does not contain compounds allowing the extraction of calcium ions and/or bivalent cations so as to allow selective extraction. As a corollary, it is also possible to use an organic phase which only allows the extraction of one or more species of divalent cations (such as calcium, magnesium, strontium, barium) and little or no monovalent cations, especially sodium.

BRIEF DESCRIPTION OF THE DRAWINGS

The invention will be better understood on reading the accompanying figures, which are provided by way of examples and are not limiting in nature, in which:

FIG. 6 is a table showing the concentrations of each ionic species in each of the flows identified in the device of Example 7 as well as the total salinity, density, temperature and flow rate of these flows when the water to be treated is seawater.

EXAMPLES

Example 1

Description of the Tested CEMs

Figure 1:
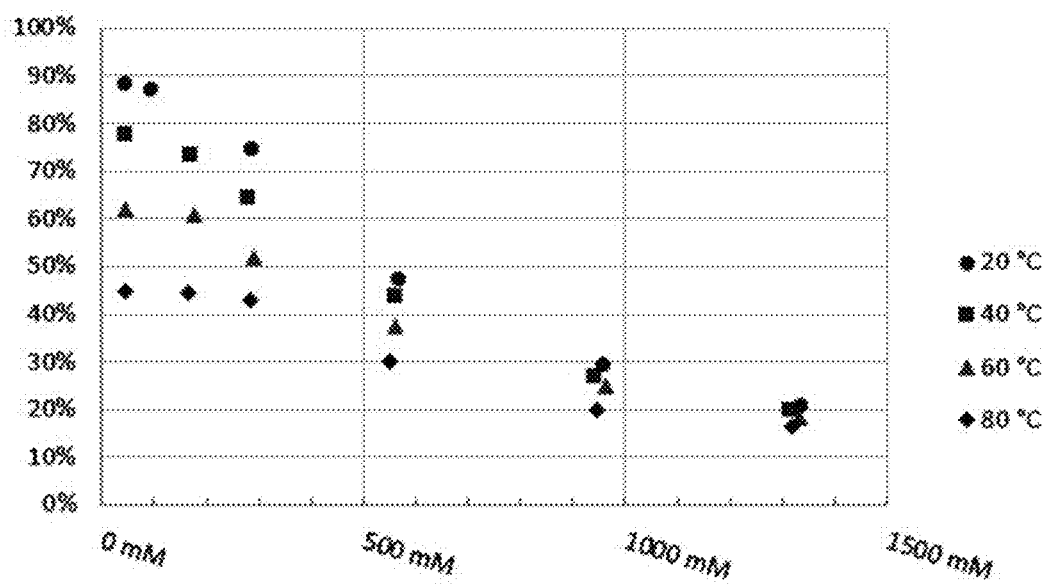
FIG. 1 is a graph showing the NaCl extraction rates in % of salt water at various concentrations (abscissa axis) and at temperatures (round: 20° C., square: 40° C., triangle: 60° C. and diamond: 80° C.) using an ASM 4/Calix[4]Est composition according to the invention, for an CEM concentration of 0.4M described in Example 6B.

Various ion-extracting compositions according to the invention have been formulated and tested. The 7 CEMs used in these compositions are the following:

| NAME | Nomenclature | Formula |
|---|---|---|
| CrownEther DB21C7 | 6, 7, 9, 10, 12, 13, 20, 21, 23, 24-Decahydrodibenzo[b,k] [1, 4, 7, 10, 13, 16, 19] heptaoxacyclohenicosine (Dibenzo-21-crown-7). CAS n° 14098-41-0, $C_{22}H_{28}O_7$, MW = 404 g/mole, MP = 107° C., S = 1.9 mMole/L (estimated at 25° C.). Log K(Na$^+$, MeOH, 25° C.) = 2.4 Log K(K$^+$, MeOH, 25° C.) = 4.19 | |
| CrownEther B15C5 | Benzo[b]-1,4,7,10,13-pentaoxa-cyclopentadecane (Benzo-15-Crown-5). CAS n° 14098-44-3, $C_{14}H_{20}O_5$, MW = 268.31 g/mole, MP = 80° C., Log P = 0.91 (Exp), S = 11.6 mMole/L (estimated at 25° C.) Log K(Na$^+$, MeOH, 25° C.) = 3.03 Log K(K$^+$, MeOH, 25° C.) = 3.93 | |
| CrownEther C15C5 | Perhydrobenzo[b]-1,4,7,10,'3-pentaoxacyclopentadecane (Cyclohexo-15-Crown-5). CAS n° 17454-48-7, $C_{14}H_{26}O_5$, MW = 274.35 g/mole, Liquid, FP = 100° C., d = 1.12 g/mL, S = 57 mMole/L (estimated at 25° C.) Log K(Na$^+$, MeOH, 25° C.) = 3.71-3.9 Log K(K$^+$, MeOH, 25° C.) = 3.96 | |
| CrownEther DC18C6 | Dicyclohexano-1,4,7,10,13,16-hexaoxacyclooctadecane (Dicyclohexano-18-crown-6). CAS n° 16069-36-6, $C_{20}H_{36}O_6$, MW = 372.51 g/mole, MP = 46-53° C., FP = 110° C., S = 36 mMole/L Log K(Na$^+$, MeOH, 25° C.) = 4.27 Log K(K$^+$, MeOH, 25° C.) = 5.97 | |
| CrownEther DB18C6 | Dibenzo[b,k]-1,4,7,10,13,16-hexaoxacyclooctadecane (Dibenzo-18-crown-6). CAS n° 14187-32-7, $C_{20}H_{24}O_6$, MW = 360.41 g/mole, MP = 163° C., Log P = 2.20 (Exp), S = 1.1 mMole/L Log K(Na$^+$, MeOH, 25° C.) = 4.50 Log K(K$^+$, MeOH, 25° C.) = 5.12 | |

| NAME | Nomenclature | Formula |
|---|---|---|
| CrownEther DB24C8 | 6, 7, 9, 10, 12, 13, 20, 21, 23, 24, 26, 27-Dodecahydrodibenzo[b,n] [1,4,7,10,13,16,19,22] octaoxacyclotetracosine (Dibenzo-24-crown-8). CAS n° 14174-09-5, $C_{24}H_{32}O_8$, MW = 448 g/mole, MP = 104° C., Log P = 2.11 (Exp), 1.865 mg/L (25° C. estimated). Log K($Na^+$, MeOH, 25° C.) = 2.35 Log K($K^+$, MeOH, 25° C.) = 3.61 | |
| Calixarene Calix[4]Est | 4-tert-Butylcalix[4]arene-O,O',O'',O'''-tetraacetic Acid Tetraethyl Ester (Calix[4]arene tetraesters, Sodium ionophore X). CAS n° 97600-39-0, $C_{60}H_{80}O_{12}$, MW = 993.27 g/mole, MP = 156-157° C. S < $1.10^{-6}$ mMole/L Log K($Na^+$, MeOH, 25° C.) = 5.0 | |
| Cryptand DC[2.2.2] | $C_{26}H_{48}N_2O_6$ (DiCyclohexanocryptand [222]) 5,6,14,15-DiCyclohexano-4,7,13,16,21,24-hexaoxa-1,10-diazabicyclo[8.8.8]hexacosane MW = 484 g/mole S = 3 mMole/L Log K($Na^+$, MeOH, 25° C.) = 6.02 Log K($K^+$, MeOH, 25° C.) = 6.92 | |
| Cryptand DB[2.2.2] | $C_{26}H_{36}N_2O_6$ (Dibenzocryptand[222]) 5,6,14,15-DiBenzo-4,7,13,16,21,24-hexaoxa-1,10-diazabicyclo[8.8.8] hexacosane CAS: 40471-97-4 MW = 472.57 g/mole S = 2.5 mMole/L Log K($Na^+$, MeOH, 25° C.) = 7.60 Log K($K^+$, MeOH, 25° C.) = 8.74 | |
| Cryptand Decyl[2.2.2] | $C_{28}H_{56}N_2O_6$ (5-Decylcryptand[222]) 5-Decyl-4,7,13,16,21,24-hexaoxa-1,10-diazabicyclo[8.8.8]hexacosane CAS: 69878-46-2 MW = 516.75 g/mole S = 0.1 mMole/L Log K($Na^+$, MeOH, 25° C.) = 7.04 Log K($K^+$, MeOH, 25° C.) = 9.0 | |

7 of the 10 CEMs presented above were solubilized in ASM 1, followed by NaCl extraction measurements. The others were solubilized in ASM 2.

Example 2

Description of the Tested ASMs

ASM 1: (3TFMPhOH)
3-(Trifluoromethyl)phenol
N° CAS: 98-17-9
$C_7H_5F_3O$,
MW=162.11 g/mole
Colorless liquid

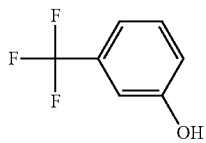 [SMILES: Oc1cccc(C(F)(F)F)c1]

| Parameters | Values | Units |
| --- | --- | --- |
| Density | 1.33 | kg/L |
| Viscosity | <50 at 25° C. | mPa · s |
| BP | 177-178 | ° C. |
| MP | −1.8 | ° C. |
| FP | 74 | ° C. |
| Log P | 2.95 | — |
| Solubility | 3.83 (estimated) | mMole/L |
| pKa | 8.68 at 25° C. | — |

ASM 2: (3TFMBnOH)
[3-(Trifluoromethyl)phenyl]methanol
N° CAS: 349-75-7
$C_8H_7F_3O$,
MW=176.14 g/mole
Odorless and colorless liquid.

| Parameters | Values | Units |
| --- | --- | --- |
| Density | 1.295 | kg/L |
| Viscosity | 9.4 at 20° C. | mPa · s |
| BP | 260 | ° C. |
| MP | <25 | ° C. |
| FP | 84 | ° C. |
| Log P | 1.74 (estimated) | — |
| Solubility | 32 | mMole/L |
| pKa | 14.74 +/− 1 | — |

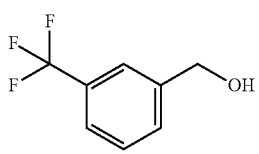 [SMILES: OCc1cccc(C(F)(F)F)c1]

ASM 3: (35TFMBnOH)
[3,5-Bis(Trifluoromethyl)phenyl]methanol
N° CAS: 32707-89-4
$C_9H_6F_6O$,
MW=244.13 g/mole
White solid.

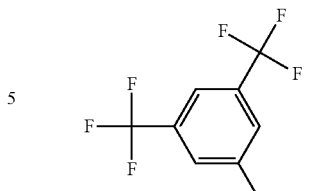

| Parameters | Values | Units |
| --- | --- | --- |
| Density | (1.433) | kg/L |
| Viscosity | — | mPa · s |
| BP | 255 | ° C. |
| MP | 55 | ° C. |
| FP | 97 | ° C. |
| Log P | 3.0 (estimated) | — |
| Solubility | 2.29 | mMole/L |
| pKa | 14.7 +/− 1 | — |

ASM 4=60% vol ASM 3+40% vol ASM 2
White, colorless liquid

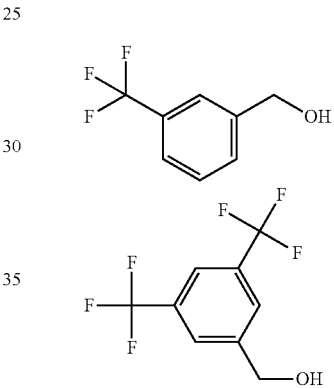

| Parameters | Values | Units |
| --- | --- | --- |
| Density | 1.389 at 20° C. | kg/L |
| Viscosity | 13.4 at 20° C. | mPa · s |
| BP | — | ° C. |
| MP | <15 | ° C. |
| FP | — | ° C. |
| Log P | 2.0 (estimated) | — |
| Solubility | 15 | mMole/L |
| pKa | 14.7 +/− 1 | — |

ASM 5: ($3C_4F_9BnOH$)
[3-(Perfluorobutyl)phenyl]methanol
N° CAS: Unknown
$C_{11}H_7F_9O$,
MW=326.16 g/mole
Odorless and colorless liquid.

| Parameters | Values | Units |
| --- | --- | --- |
| Density | 1.488 | kg/L |
| Viscosity | 40 at 20° C. | mPa · s |
| BP | at mmHg | ° C. |
| MP | <15 | ° C. |
| FP | — | ° C. |
| Log P | 4.57 (estimated) | — |

| Parameters | Values | Units |
|---|---|---|
| Solubility | <0.077 (not detected in UV-visible) | mMole/L |
| pKa | 14.7 +/− 1 | — |
| Density | 1.585 | kg/L |
| Viscosity | — | mPa · s |
| BP | at mmHg | ° C. |
| MP | — | ° C. |
| FP | — | ° C. |
| Log P | 5.75 (estimated) | — |
| Solubility | <0.07 | mMole/L |
| pKa | 14.25 +/− 1 | — |

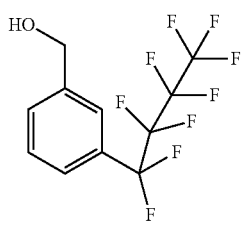 [SMILES: OCc1cccc(C(F)(F)C(F)(F)C(F)(F)C(F)(F)F)c1]

ASM 6: (3,5-C$_3$F$_7$BnOH)
[3,5-(Perfluoropropyl)phenyl]methanol
N° CAS: Unknown
C$_{13}$H$_6$F$_{14}$O,
MW=444.16 g/mole

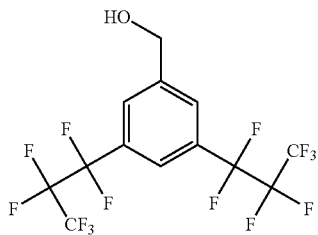 [SMILES: OCc1cc(C(F)(F)C(F)(F)C(F)(F)F)cc(C(F)(F)C(F)(F)C(F)(F)F)c1]

In the tables of data above the acronyms BP, MP and FP designate:
BP=boiling point
MP=melting point
FP=flash point

Example 3

The compound of formula ASM5 was synthesized as follows:
First Step

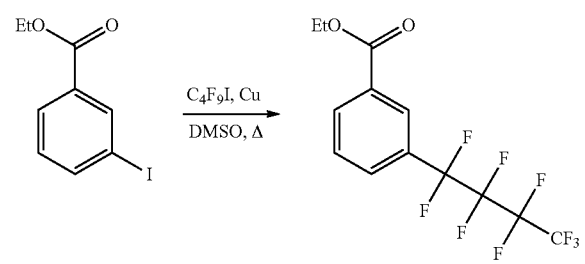 [SMILES: CCOC(=O)c1cccc(I)c1 ; CCOC(=O)c1cccc(C(F)(F)C(F)(F)C(F)(F)C(F)(F)F)c1]

A solution of ethyl 3-iodobenzoate (207.9 g, 753.2 mmol, 1.0 eq.), Copper powder (239.3 g, 3.766 mol, 5.0 eq.) and 450 mL of DMSO, is degassed and then is put under an argon atmosphere. The mixture is then brought to 130° C. and then a solution of 1-iodoperfluorobutane (181.5 mL, 1.054 mol, 1.4 eq) is added dropwise over 30 minutes. The reaction mixture is stirred at 130° C. for 5 h under an argon atmosphere. After returning to room temperature, 2 L of ethyl acetate and 1 L of water are added. The mixture is then filtered through silica (Celite). The organic phase is washed with water (2×1 L), dried over sodium sulphate, filtered and then concentrated under reduced pressure to give crude ethyl 3-(perfluorobutane)benzoate (269.0 g, 730.6 mmol, 97% light brown liquid).

$^1$H NMR (CDCl$_3$, 300 MHz): δ (ppm)=1.42 (t, $^3$J=7.1 Hz, 3H), 4.44 (q, $^3$J=7.1 Hz, 4H), 7.61 (t, $^3$J=8.0 Hz, 1H), 7.78 (d, $^3$J=7.7 Hz, 1H), 8.24-8.30 (m, 2H).

Second Step

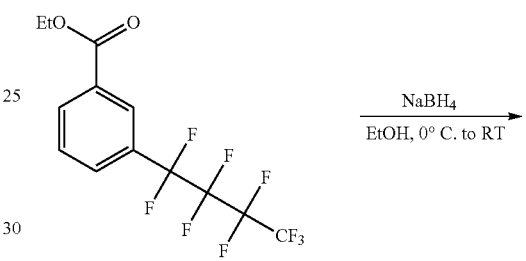

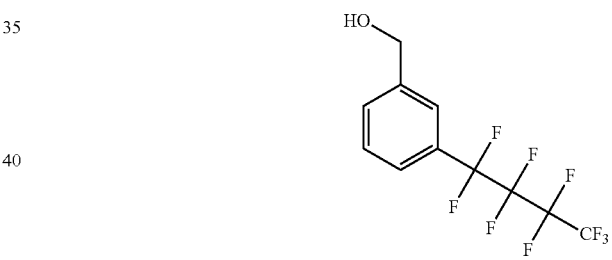

To a solution, cooled with an ice bath, of ethyl 3-(perfluorobutane)benzoate (269.0 g, 730.6 mmol, 1.0 eq.) and of 500 mL of ethanol, is added in small portions sodium borohydride (82.9 g, 2.192 mol, 3.0 eq). The temperature is controlled and must be below 20° C. Once the addition is completed, the reaction mixture is stirred at room temperature for 15 h. After stirring is over, a saturated solution of NH$_4$Cl (2 L) is added at cold temperature and then diluted with 2 L of ethyl acetate. The aqueous phase is extracted with ethyl acetate (1×1 L) and the organic phases are washed with i) a saturated solution of NH$_4$Cl (1×1 L) and ii) with water (1×1 L). After drying over sodium sulphate and filtration, the organic phase is concentrated under reduced pressure to give crude [(3-perfluorobutyl)phenyl]methanol (228.9 g, 701.8 mmol, 96%, light brown liquid).

The crude compound was purified by vacuum distillation (P=5 mmbars, BP=98-102° C.) to give [(3-perfluorobutyl)phenyl]methanol (162.5 g, 498.2 mmol, 68%, colorless liquid).

$^1$H NMR (CDCl$_3$, 300 MHz): δ (ppm)=1.72 (br s, 1H), 4.79 (s, 2H), 7.49-7.53 (m, 2H), 7.56-7.62 (m, 2H).

Example 4

The compound of formula ASM6 was synthesized as follows:

First Step

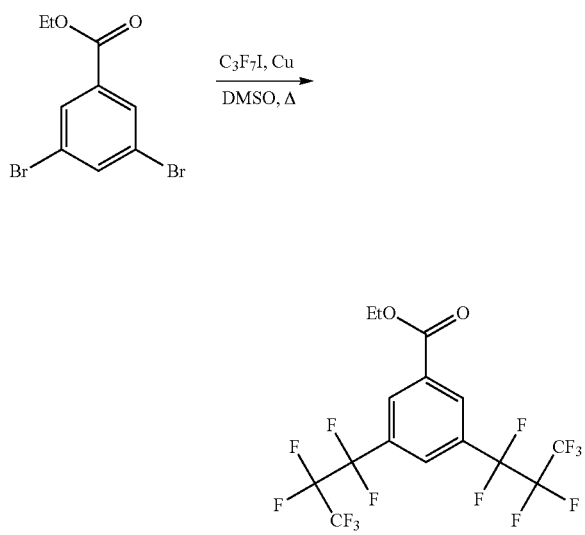

A few crystals of iodine are added to a suspension of copper powder (10.32 g, 162.4 mmol, 5.0 eq.) and acetone (50 mL). After stirring for 30 minutes, the liquid phase is removed by filtration and the copper is washed with a solution of gaseous hydrochloric acid in acetone (60 mL) and then with acetone (60 mL). The activated copper is introduced into a solution of ethyl 3,5-dibromobenzoate (10.0 g, 32.5 mmol, 1.0 eq.) and 500 mL of DMSO. The suspension is degassed and then placed under an argon atmosphere. The mixture is then brought to 130° C. A solution of 1-iodoperfluoropropane (13.2 mL, 90.9 mmol, 2.8 eq) is added dropwise over 30 minutes. The reaction mixture is stirred at 130° C. for 5 h under an argon atmosphere. After returning to room temperature, 50 mL of ethyl acetate and 50 mL of water are added. The mixture is then filtered through celite. The organic phase is washed with water (2×50 mL), dried over sodium sulphate, filtered and then concentrated under reduced pressure to give crude ethyl 3,5-bis(perfluoropropane) benzoate (15.46 g, 31.8 mmol, 98%, yellow solid).

$^1$H NMR (CDCl$_3$, 300 MHz): δ (ppm)=1.45 (t, $^3$J=7.1 Hz, 3H), 4.46 (q, $^3$J=7.1 Hz, 4H), 7.96 (br. s, 1H), 8.48 (br. s, 2H).

Second Step

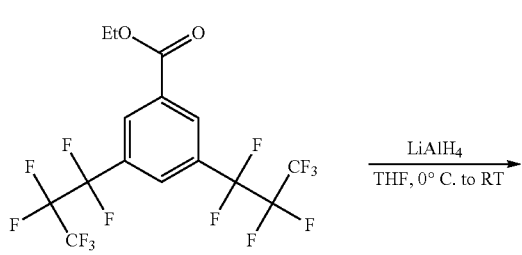

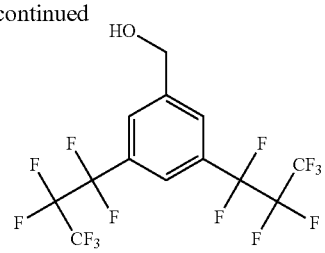

A solution of ethyl 3,5-bis(perfluorobutane) benzoate (15.46 g, 31.8 mmol, 1.0 eq.) and 100 mL of anhydrous THF is added dropwise to a suspension of LiAlH$_4$ (1.81 g, 47.7 mmol, 1.5 Eq.) and of anhydrous THF (10 mL) under an argon atmosphere and at 0° C. After the addition was complete, the reaction mixture was stirred at room temperature (RT) for 5 h. Then, 10 mL of ethyl acetate is added very slowly. After 15 min, 10 mL of a 10% sulfuric acid solution is cautiously added at 0° C., then the reaction medium is stirred for 20 min. The aqueous layer was extracted with ethyl acetate (3×50 mL). The organic phases are combined, washed with saturated NaCl solution (1×50 mL), dried over magnesium sulphate, filtered and then concentrated under reduced pressure to give a pale yellow solid. This solid is recrystallized from hexane to give [3,5-bis(perfluorobutyl)] phenylmethanol (12.95 g, 29.3 mmol, 92%, liquid).

$^1$H NMR (CDCl$_3$, 300 MHz): δ (ppm)=4.88 (s, 2H), 7.70 (br. s, 1H), 7.82 (br. s, 2H).

Example 5

Compositions Comprising a Fluorinated ASM of the Phenolic Type: 3TFMPhOH with Various CEMs 3-(Trifluoromethyl)phenol was purchased from AlfaAesar, and has a purity of 98+%. It was used as it was.

Dibenzo-18-crown-6 was purchased from TCI Chemicals, and has a purity of >99%, it was used as it was.

To 3 mL of 3-(trifluoromethyl)phenol, was added 217 mg of Dibenzo-18-crown-6 in order to obtain a formulation with 0.2 mole/L of DB18C6. This sealed formulation was then orbitally stirred at 500 rpm overnight after 1 mL of distilled water was added twice to allow water saturation of the whole.

The next morning, an aqueous 0.2 mol/L NaCl solution was prepared from twice distilled water, while the formulation that was stirred overnight was allowed to stand for decantation. A clear decantation of the two colorless phases is obtained in a few minutes. 3 mL of the organic extraction solution is then removed and transferred to a flask containing 3 mL of this salt water containing 0.2 M NaCl, then the flask is sealed and orbitally stirred (usually 500 rpm), for 3 hours and at room temperature. It is verified that droplets of the order of 1-2 mm are present in quantity at the selected stirring speed (400 to 900 rpm).

After stirring for 2 hours, stirring is stopped and the whole is left to stand for decantation for at least 10 minutes until the two phases are completely separated. The upper aqueous phase is then removed and then stirred and diluted for analysis of its salinity by a Metrohm Ion Chromatography incorporating a suitable cation analysis column and a suitable anion analysis column. Similarly, the initial aqueous solution of 0.2M NaCl is also analyzed by this ion chromatography equipment to determine its relative concentration of sodium and chlorides.

Results:

| ASM:3TFMPhOH | CEM:DB18C6 0.2M | [Na+] mmol/L | [Cl−] mmol/L | Mean mmol/L |
|---|---|---|---|---|
| Water to be treated 0 | NaCl 0.2M | 188.77 | 193.33 | 191.05 |
| Treated water | NaCl 0.125M | 130.6 | 119.4 | 125.0 |
| Extraction rate at 23° C. | $([NaCl]_{aq0} - [NaCl]_{aq})/[NaCl]_{aq0}$ | 30.8% | 38.8% | 34.6% |

This composition is capable of extracting, by direct contact, at iso-volume and at ambient temperature, slightly more than a third of the NaCl present in the water. In addition, slightly more than one-third of the extractant molecules of sodium are in complexed form. Thus, thanks to the presence of the ASM, we observe a 34.6% extraction, where we do not exceed 1.6% extraction by replacing this ASM by dichloromethane.

The same procedure as described above for DB18C6 was applied to the other CEMs described in Example 1. The results of the chromatographic analysis are as follows:

| ASM:3TFMPhOH | CEM:DB21C7 0.2M | [Na+] mmol/L | [Cl−] mmol/L | Mean mmol/L |
|---|---|---|---|---|
| Water to be treated 0 | NaCl 0.2M | 183.77 | 196.29 | 190.03 |
| Treated water | NaCl 0.16M | 166.4 | 155.7 | 161.1 |
| Extraction rate at 23° C. | $([NaCl]_{aq0} - [NaCl]_{aq})/[NaCl]_{aq0}$ | 9.4% | 20.7% | 15.2% |

| ASM:3TFMPhOH | 0.2M | mmol/L | mmol/L | mmol/L |
|---|---|---|---|---|
| | CEM:B15C5 | [Na+] | [Cl−] | Mean |
| Water to be treated 0 | NaCl 0.2M | 188.77 | 193.33 | 191.05 |
| Treated water | NaCl 0.16M | 156.4 | 169.1 | 162.7 |
| Extraction rate at 23° C. | $([NaCl]_{aq0} - [NaCl]_{aq})/[NaCl]_{aq0}$ | 17.2% | 12.5% | 14.8% |

| ASM:3TFMPhOH | CEM:C15C5 0.2M | [Na+] mmol/L | [Cl−] mmol/L | Mean mmol/L |
|---|---|---|---|---|
| Water to be treated 0 | NaCl 0.2M | 183.77 | 196.29 | 190.03 |
| Treated water | NaCl 0.14M | 145.2 | 136.0 | 140.6 |
| Extraction rate at 23° C. | $([NaCl]_{aq0} - [NaCl]_{aq})/[NaCl]_{aq0}$ | 21.0% | 30.7% | 26.0% |

| ASM:3TFMPhOH | CEM:DC18C6 0.2M | [Na+] mmol/L | [Cl−] mmol/L | Mean mmol/L |
|---|---|---|---|---|
| Water to be treated 0 | NaCl 0.2M | 192.45 | 182.55 | 187.50 |
| Treated water | NaCl 0.13M | 136.4 | 127.2 | 131.8 |
| Extraction rate at 23° C. | $([NaCl]_{aq0} - [NaCl]_{aq})/[NaCl]_{aq0}$ | 29.1% | 30.3% | 29.7% |

| ASM:3TFMPhOH | CEM:DB24C8 0.2M | [Na+] mmol/L | [Cl−] mmol/L | Mean mmol/L |
|---|---|---|---|---|
| Water to be treated 0 | NaCl 0.2M | 192.45 | 182.55 | 187.50 |
| Treated water | NaCl 0.12M | 124.0 | 114.9 | 119.5 |
| Extraction rate at 23° C. | $([NaCl]_{aq0} - [NaCl]_{aq})/[NaCl]_{aq0}$ | 35.5% | 37.1% | 36.3% |

| ASM:3TFMPhOH | CEM:Calix[4]Est 0.2M | [Na+] mmol/L | [Cl−] mmol/L | Mean mmol/L |
|---|---|---|---|---|
| Water to be treated 0 | NaCl 0.2M | 192.45 | 182.55 | 187.50 |
| Treated water | NaCl 0.045M | 48.1 | 41.9 | 45.0 |
| Extraction rate at 23° C. | $([NaCl]_{aq0} - [NaCl]_{aq})/[NaCl]_{aq0}$ | 75% | 77% | 76% |

These results show that the extraction rate of the NaCl is strongly dependent on the affinity of the CEM, that is to say of the extractant, for the Na+ cation.

In fact, taking into account the published complexing constants for all of these CEM extractants for sodium, in methanol at 25° C., it is observed a linear correlation in the first part, and then, surprisingly, more strongly growing at the moment when the affinity of the CEM for the sodium in the water exceeds Log K of 1. Moreover this same tendency is also obtained in extraction of KCl or of $Na_2SO_4$.

| CEM | DB21C7 | B15C5 | C15C5 | DC18C6 | DB18C6 | Calix4Est | DB24C8 |
|---|---|---|---|---|---|---|---|
| Log K (Na+) MeOH à 25° C. | 2.4 | 3.03 | 3.71–3.9 | 4.27 | 4.36–4.49 | 5.0–5.7 | 2.25 |
| Extraction rate at 23° C. | 15.2% | 14.8% | 26.0% | 29.7% | 34.6% | 76% | 36.3% |

Only the DB24C8 does not comply with this rule. An explanation could come from the fact that this crown ether is very broad. Indeed, an absorption of two $Na^+$ cations has already been observed for these macrocycles. However, the complexing constant of 2.25 for this DB24C8 compound could correspond to the case where only one cation is complexed. A complexing constant twice as high as that published for DB24C8 (ie 4.5) would then restore the aforementioned correlation. Thus a CEM presenting at the same time:

- a complexing constant for sodium, in water at 25° C., greater than or equal to 1, and

- a complexing constant for sodium, in ethanol at 25° C., greater than or equal to 4, preferably greater than 4.75, makes it possible to have particularly high levels of ion extraction, and in particular for salts such as NaCl, KCl or $Na_2SO_4$.

Example 6

Compositions Containing a Fluorinated ASM of Methanolic Phenyl Type (ASM 2 and 5) or a Mixture of these Compounds (ASM 4 and 7) with the CEM: Calix 4 Est

Example 6A

Composition ASM 2/Calix[4]Est for Extraction of NaCl

Compound ASM 2 was purchased from Fluorochem (97% purity) and used as it was.

The composition ASM 2/Calix[4]Est is prepared, tested and analyzed according to the same protocol as that described in the preceding Example 5.

Results for composition ASM 2/Calix[4]Est:

| ASM:3TFMBnOH | CEM:0.2M Calix[4]Est | [Na+] mmol/L | [Cl−] mmol/L | Mean mmol/L |
|---|---|---|---|---|
| Water to be treated 0 | NaCl 0.2M | 176.96 | 208.34 | 192.65 |
| Treated water Extraction rate at 23° C. | NaCl 0.08M ([NaCl]$_{aq0}$ − [NaCl]$_{aq}$)/ [NaCl]$_{aq0}$ | 80.8 54.3% | 78.8 62.2% | 79.8 58.6% |

Example 6B

Composition ASM 4/Calix [4]Est for Extraction of NaCl

ASM 4 is a mixture of ASM 2 and ASM 3 (solid under normal temperature and pressure conditions). 30.4 mL of ASM 4 were formulated by adding 12.16 mL of ASM 2 to 26.14 g of ASM 3. After stirring and dissolving ASM 2, 6.04 g Calix[4]Est is added and solubilized rapidly by means of a slight heating to 40° C. A dilation of the formulation is observed after solubilization of Calix[4]Ester and saturation in water. These compositions were tested and analyzed according to the same procedure as that described in Example 5.

Results for composition ASM 4/Calix[4]Est:

| ASM 4:3TFMBnOH + 35TFMBnOH | CEM:Calix[4]Est 0.2M | [Na+] mmol/L | [Cl−] mmol/L | Mean mmol/L |
|---|---|---|---|---|
| Water to be treated 0 | NaCl 0.2M | 212.71 | 205.48 | 209.09 |
| Treated water Extraction rate at 23° C. | NaCl 0.04M ([NaCl]$_{aq0}$ − [NaCl]$_{aq}$)/ [NaCl]$_{aq0}$ | 42.1 80.2% | 46.5 77.4% | 44.3 78.8% |

This particular example was reproduced a second time to give an average extraction performance at 78.9%, thus consistent.

The presence of a second trifluoromethyl in the meta position of the alcohol function has a very favorable effect on the extraction of the NaCl by allowing a better solvation of the anions.

The graph of FIG. 1 represents the extraction rates obtained by an ASM 4 and Calix4Est composition (0.4 M) for salt water (NaCl) of various salinities and at variable temperatures ranging from ambient temperature to 80° C. and iso-volume Water/(ASM 4/Calix[4]Est) Composition.

The extraction performance is quite remarkable, with NaCl extraction rates ranging from 90% for the lowest concentrations to 15% for the highest concentrations, all at iso-volume water/solvent with a decrease of Extraction rate of about one third at 60° C. compared to 20° C.

For this ASM 4/Calix[4]Est composition, it is calculated via these results that the enthalpic interactions developed are of the order of 33 kJ/mole of displaced salts. Thus, for a displacement of 36 g NaCl per liter of water (standard seawater concentration), a basic energy of only 21 kJ/kg of desalted water is required. The latent heat of vaporization of water being 2319 kJ/kg at 75° C., the energy consumed during the implementation of the method according to the invention is 100 times less than that required for the evaporation of water.

Figure 2:
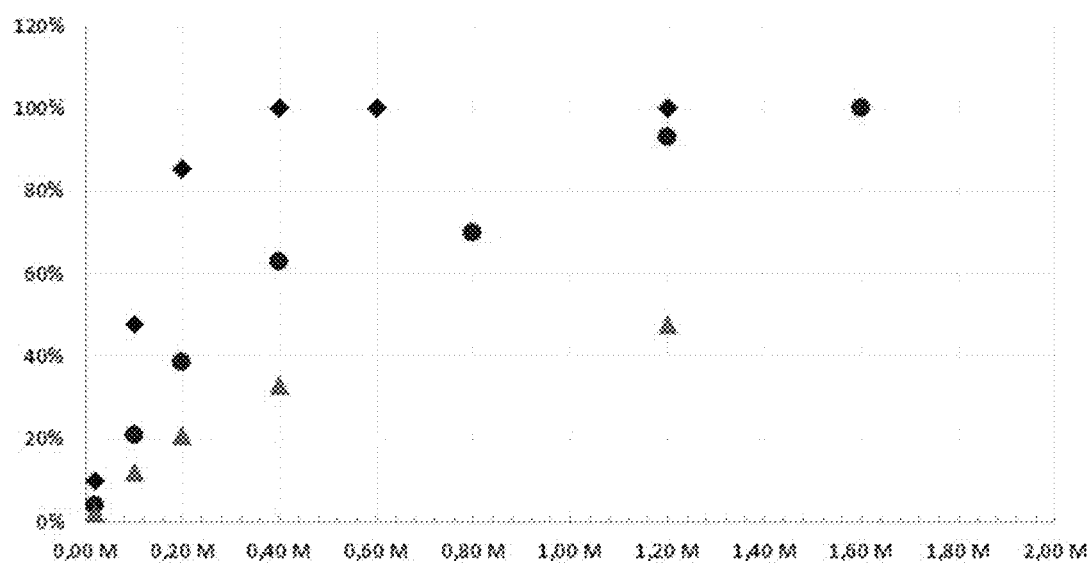
FIG. 2 is a graph showing, for ASM 4/Calix[4]Est compositions of Example 6B (diamond: 0.2M, round: 0.4M and triangle: 0.8M of CEM), the % loading rates of CEM in NaCl for various initial concentrations of NaCl in Mol/L and at room temperature.

The graph of FIG. 2 shows the loading rate of the CEM, Calix[4]Est with NaCl, as a function of the concentration of CEM (diamond: 0.2M, round: 0.4M and triangle 0.8M) when it is under extraction with salt water of various concentrations. To obtain an optimum loading rate (close to 100%) at the end of the extraction/absorption phase for salt water at salinities close to the typical salinity of seawater (0.6 M), a concentration between 0.2 M and 0.4 M of Calix[4]Est is to be preferred.

EXAMPLE 6C

Composition ASM 4/Calix[4]for the Extraction of Na$_2$SO$_4$

Figure 3:
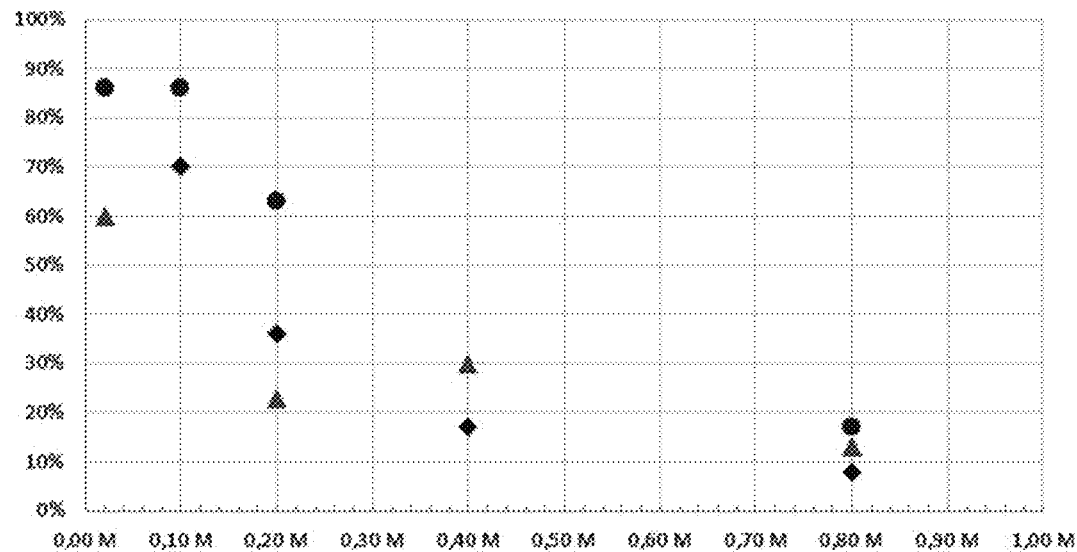
FIG. 3 is a graph showing the extraction rates in % $Na_2SO_4$ of a water containing it at various initial concentrations and at ambient temperature by using an ASM4/Calix[4]Est composition at various concentrations (triangle: 0.2M, diamond: 0.4M and round: 0.8M) according to the invention described in EXAMPLE 6C.

The extraction of Na$_2$SO$_4$ was also carried out with the composition ASM 4/Calix[4]Est previously described for various concentrations of Calix[4]Est (triangle: 0.2M, diamond: 0.4M and round 0.8M). The graph of FIG. 3 represents the extraction rates of this salt which have been obtained for waters of different Na$_2$SO$_4$ concentrations following the protocol described above. It appears that a greater concentration of CEM allows improved extraction of Na$_2$SO$_4$.

Although the sulphates belong to the most hydrophilic anions, we again observe a good extraction of these salts over all the concentrations tested.

Example 6D

Composition ASM 5/Calix[4]Est for Extraction of NaCl

ASM 5 compound was synthesized according to the method described in Example 3 and used as it was.

The ASM 5/Calix[4]Est composition is prepared, tested and analyzed according to the same protocol as that described in Example 5 except that the orbital stirring used was 900 rpm because of a higher viscosity of this formulation.

Results for composition ASM 5/Calix[4]Est:

| ASM 5:3C4F9BnOH | CEM:Calix[4]Est 0.2M | [Na+] mmol/L | [Cl−] mmol/L | Mean mmol/L |
|---|---|---|---|---|
| Water to be treated 0 | NaCl 0.2M | 189.17 | 191.24 | 190.20 |
| Treated water Extraction | NaCl 0.086M ([NaCl]$_{aq0}$ − | 86.65 54.2% | 86.44 54.8% | 86.55 54.5% |

| ASM 5:3C4F9BnOH | CEM:Calix[4]Est 0.2M | [Na+] mmol/L | [Cl−] mmol/L | Mean mmol/L |
|---|---|---|---|---|
| rate at 23° C. | $[NaCl]_{aq}/$ $[NaCl]_{aq0}$ | | | |

A slightly lower NaCl extraction rate is obtained when compared to ASM 2 but for a product with a much lower solubility in water (<0.077 vs. 32 mMole/L).

Example 6E

Composition ASM 7/Calix[4]Est for Extraction of NaCl

ASM 7 is a mixture of 70% ASM 5 and 30% ASM 6 v/v. It was obtained with the same process as for ASM 4, after recalculation of the masses of compounds to be brought into contact.

These compositions were synthesized, formulated, tested and analyzed according to the same procedure as that described in Example 5.

Results for composition ASM 7/Calix[4]Est:

| ASM 7:3C4F9BnOH + 35C3F7BnOH | MEC:Calix[4]Est 0.2M | [Na+] mmol/L | [Cl−] mmol/L | Mean mmol/L |
|---|---|---|---|---|
| Water to be treated 0 | NaCl 0.2M | 212.7 | 205.5 | 209.1 |
| Treated water | NaCl 0.05M | 54.2 | 50.2 | 52.2 |
| Extraction rate at 23° C. | $([NaCl]_{aq0} - [NaCl]_{aq})/$ $[NaCl]_{aq0}$ | 74.5% | 75.6% | 75% |

A slightly lower level of NaCl extraction is obtained when compared to ASM 4 but for a product with a much lower water solubility (<0.07 vs 15 mMole/L).

Example 7

Method and Device

Figure 4:
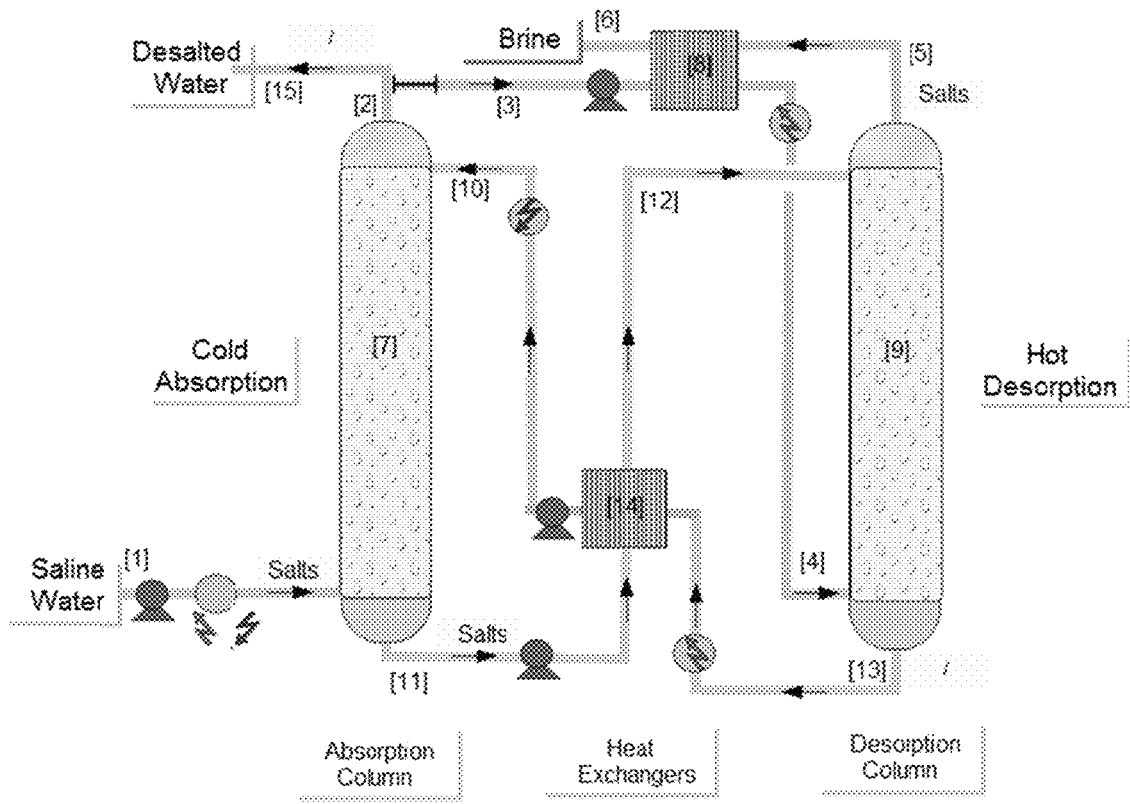
FIG. 4 is a schematic representation of example 7 with a device according to the invention making it possible to implement the method according to the invention.
Figure 5:
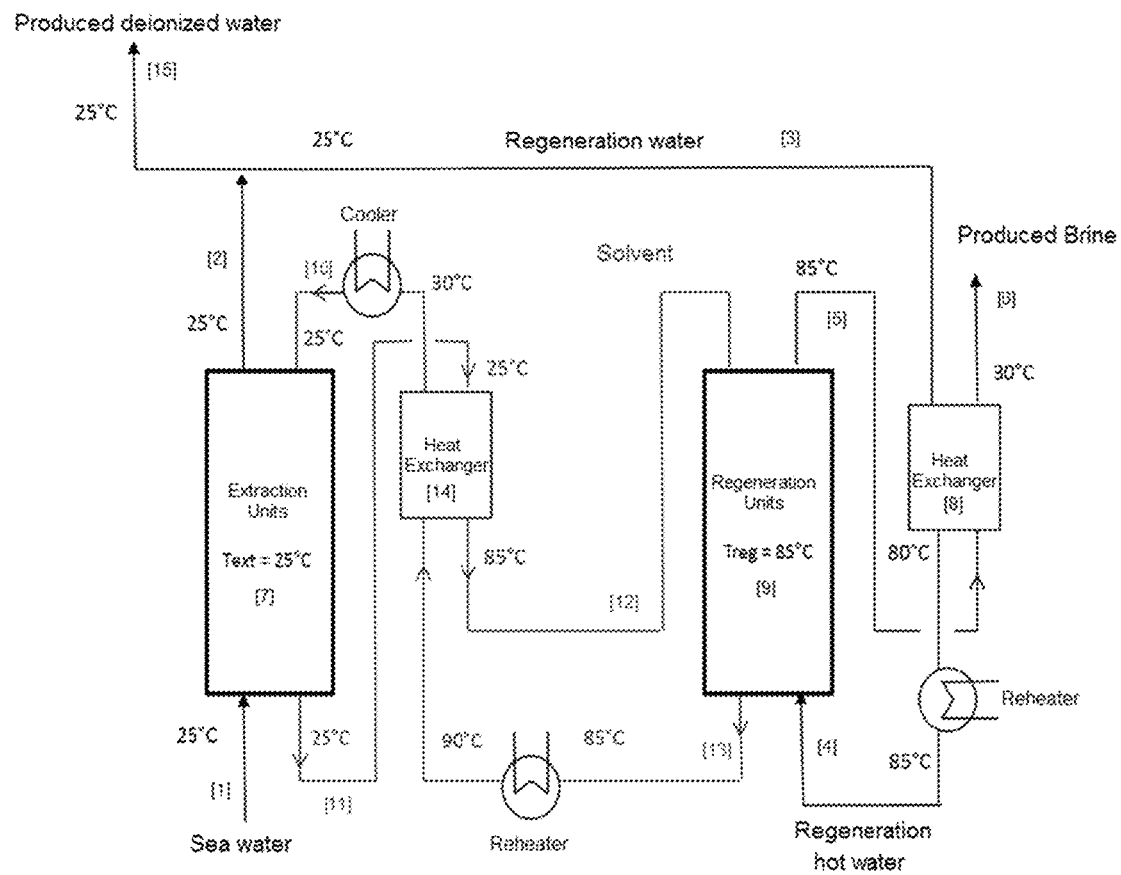
FIG. 5 is another schematic representation of the example of FIG. 4 showing an example of the operating temperature of the various parts of the device.
Figure 6:
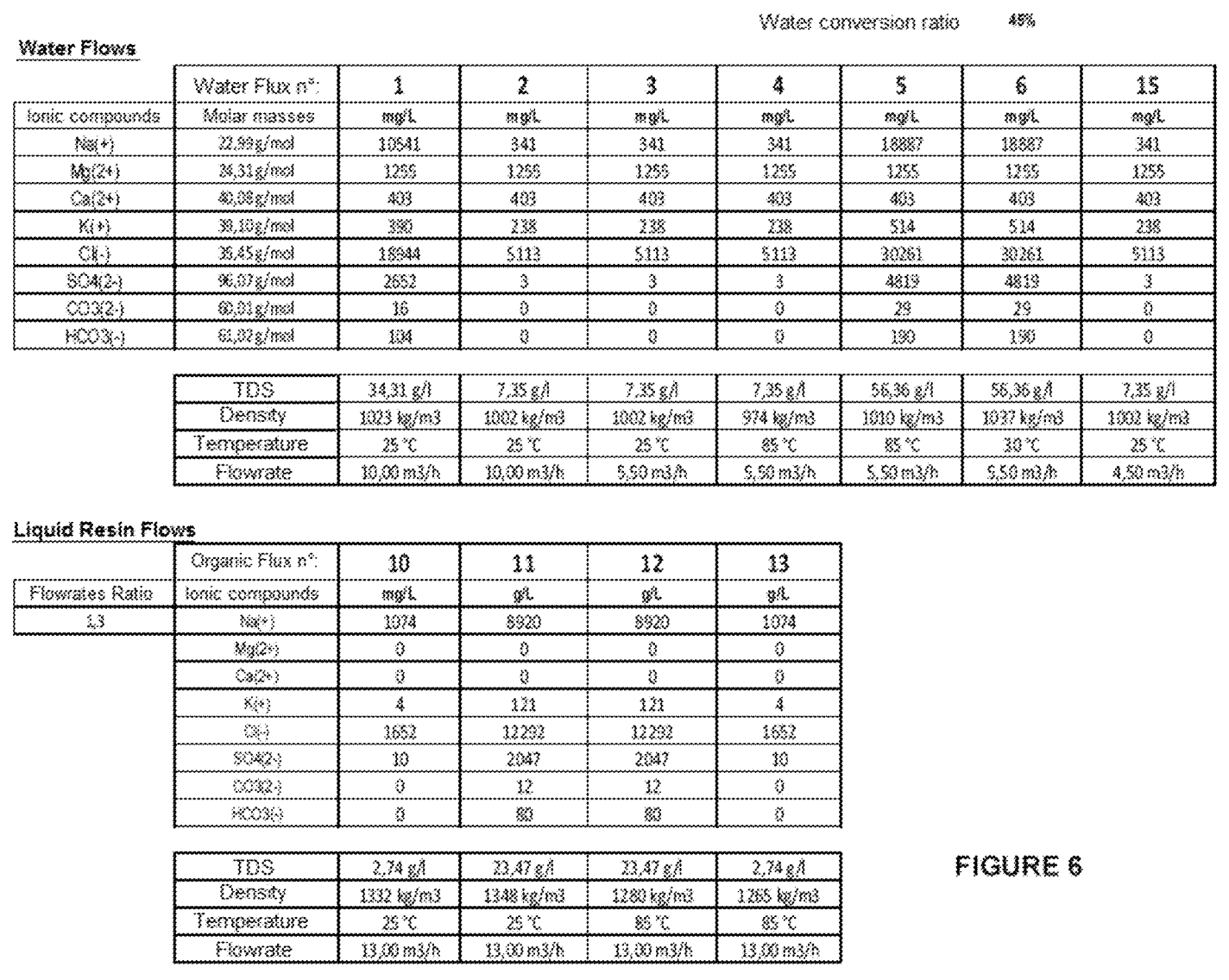

An example of a device according to the invention making it possible to implement the method according to the invention is shown in FIGS. 4 and 5. This example relates to a system for cold extraction/absorption of ions associated to a system of hot de-extraction/desorption of ions, both in liquid phases. FIG. 5 includes an indication of the temperatures of the liquids at each step and for each flow of the device. FIG. 6 is a table showing the concentrations of each ionic species in each of the identified flows as well as the total salinity, density, temperature and flow rate of these flows when the water to be treated is sea water.

Reactor

The device comprises a first reactor (7) and a second reactor (9) allowing mixing of the organic phase and the aqueous phase and the decantation of the liquids. This mixing allows the contact between the two phases and therefore the exchange of ions. The more intimate the contact is, the more important the exchange of ions is.

Such reactors (7) and (9) may comprise liquid-liquid extraction/absorption gravitational columns (as shown in FIG. 4 where reactors (7) and (9) are advantageously of similar construction). Alternatively, the reactor (7) and/or the reactor (9) may be chosen from mixer-settlers and/or centrifugal extractors/settlers.

These reactors (7) and (9) can thus comprise stirring means (for example at least one stirrer) enabling the mixer to ensure better pumping action by axial or radial flow and a turbulence action with more or less shear.

These stirring means integrate moving elements, such as propellers or other rotating elements for shear and/or turbulence. They may also comprise centrifuging means and/or a centrifuge, for example comprising a centrifugal settler.

Alternatively or cumulatively, they may contain static shear means, such as the presence of structured or not structured packing inside the reactor, acting as a stop to oppose the progression of the liquid and resulting in turbulence and/or shear of the liquid present within the reactor.

Method: Water Treatment

In the example shown in FIGS. 4 and 5, the absorption column (7) therefore permits the mixing of a hydrophobic organic liquid phase according to the invention which is chosen so that it has a higher density than the water to be treated and the produced brine.

Thus, when the reactor is a column, the two liquid phases are advantageously introduced into vertically opposite parts of the column (7) where they therefore circulate counter to each other by a simple gravitational effect. The opening allowing the introduction of the denser phase is advantageously positioned in the upper part of the column (7) but below the settling zone constituted by the upper end of the column (7). Similarly, the opening allowing the introduction of the less dense phase is advantageously positioned in the lower part of the column (7) but above the settling zone which constitutes the lower end of the column (7).

Stirring means as described above are advantageously included in the reactor (7) in order to allow the intimate mixing of the two liquid phases.

Saline water to be treated (1) is advantageously sea water and is introduced, for example by means of a pump, to the column (7) where the ions dissolved in the water are transferred totally or partially to the organic phase, namely, in this particular case, calix[4]Est dissolved at a level of 0.3M in ASM 6. The organic phase which is not miscible with water, therefore contains ion solvating molecules, with high affinity for at least some of the ions to be transferred. For this particular example, where the organic phase not charged with ions (10) introduced at the top of the column is denser than the water to be treated (1), the uncharged organic phase (10) flows down the column and gets charged with ions extracted from the saline water to be treated (1) to reach the lower end of the column (7) where it accumulates by decantation after coalescence. Conversely, the water to be treated (1) injected into the lower part of the column (7) flows up by differential density (Archimedes principle) while gradually transferring its ions to the descending organic phase, to reach the upper end of the column (7) as treated water (2) or desalted water. This treated water is desalted and/or deionized in whole or in part, that is to say that it has lost all or at least some of the salts and/or the ions constituting these salts, which where dissolved before its passage into the reactor (7). For example, this water is dechlorinated or decarbonated.

Method: Heating the Organic Phase

The organic phase charged with ions (11) is then pumped to a first heat exchanger (14) in order to be heated to a sufficient temperature (cf. FIG. 5) in order to allow the charged organic phase (11) to be discharged from the ions extracted from the water to be treated (1) in the preceding step in the reactor (7). The charged and heated organic phase

(12) is then introduced into the upper part of the second reactor (9) so as to be brought into contact with hot treated water (4).

Second Reactor

As previously described when the reactor is a column, as in this example, the two liquid phases are advantageously introduced into vertically opposite parts of the column (9) where they thus circulate counter to each other by a simple gravitational effect. The opening allowing the introduction of the denser phase is advantageously positioned in the upper part of the column (9) but below the settling zone constituted by the upper end of this column (9). Similarly, the opening allowing the introduction of the less dense phase is advantageously positioned in the lower part of the column (9) but above the settling zone which constitutes the lower end of this column (9).

Stirring means as described above are advantageously included in the reactor (9) in order to allow the intimate mixing of the two liquid phases.

Method: Organic Phase Recycle

The hot treated water (4) advantageously comes from the treated water (2) obtained at the end of its treatment in the reactor (7) and a part of which is directed by the pipe (3) to a second heat exchanger (8) to be heated therein. The other portion of the treated water (15) may be used.

This hot treated liquid water (4) is therefore injected into the lower part of the column (9) and mixed with the charged and hot organic liquid phase (12). This hot liquid water (4) ascends by differential density (Archimedes principle) while gradually charging due to the temperature of the descending organic phase, to reach the upper end of the column (9) as ion-charged water (5). This ion-charged water (5) preferably has an ion concentration higher than that present in the water to be treated (1) and is then referred to as brine (or concentrate). This brine or concentrate (5) is evacuated after settling and is directed to the heat exchanger (8) in order to be cooled as brine (6). The charged organic phase (12) arriving at the top of the column (9) is denser than the hot regeneration water (4), the charged and hot organic phase (12) flows down the column (9) while gradually transferring its extracted ions to the hot liquid treated water (4) to reach the lower end of the column (9) where it accumulates by settling after coalescence. This regenerated organic phase (13) having transferred to the hot regeneration water (4) the salts (or ions) extracted in column (9) is then cooled by passage through the heat exchanger (14) to be redirected (for example by means of a pump) to the upper part of the first reactor (7) in order to be introduced therein and thus recycled as uncharged organic phase (10).

Organic Phase and Operating Temperature

In the method and the device according to the invention, controlling the temperature of the medium of the first and second reactors (7) and (9) is an important factor in ensuring optimized operation thereof. Also, temperature control means are advantageously included in the device according to the invention in order to control and possibly modify the temperature of the latter. These may include temperature measuring means (such as thermometers) and/or heating means (eg a heat source) or cooling means (eg, a cooler).

In the particular example described in FIG. 4, such means may advantageously be disposed in or form part of:

1—a pipe to feed the water to be treated (1) to the first reactor (7),
2—a pipe to feed the hot ion-charged organic phase (12) from the exchanger (14) to the second reactor (9),
3—a pipe to feed the hot regeneration water (4) from the heat exchanger (8) to the second reactor (9), and/or
4—a pipe to feed the regenerated organic phase (10) from the heat exchanger (14) to the first reactor (7).

In the second or third case mentioned above, the control means advantageously comprise heating means. In the fourth of the above mentioned cases, the control means may advantageously comprise cooling means.

Thus, the method according to the invention makes it possible to obtain a brine that is more concentrated in salts (ions) than the water to be treated due to the intrinsic properties for extraction/ion absorption of the non water miscible organic phase, which depend on the considered operating temperature.

Example 8

Figure 7:
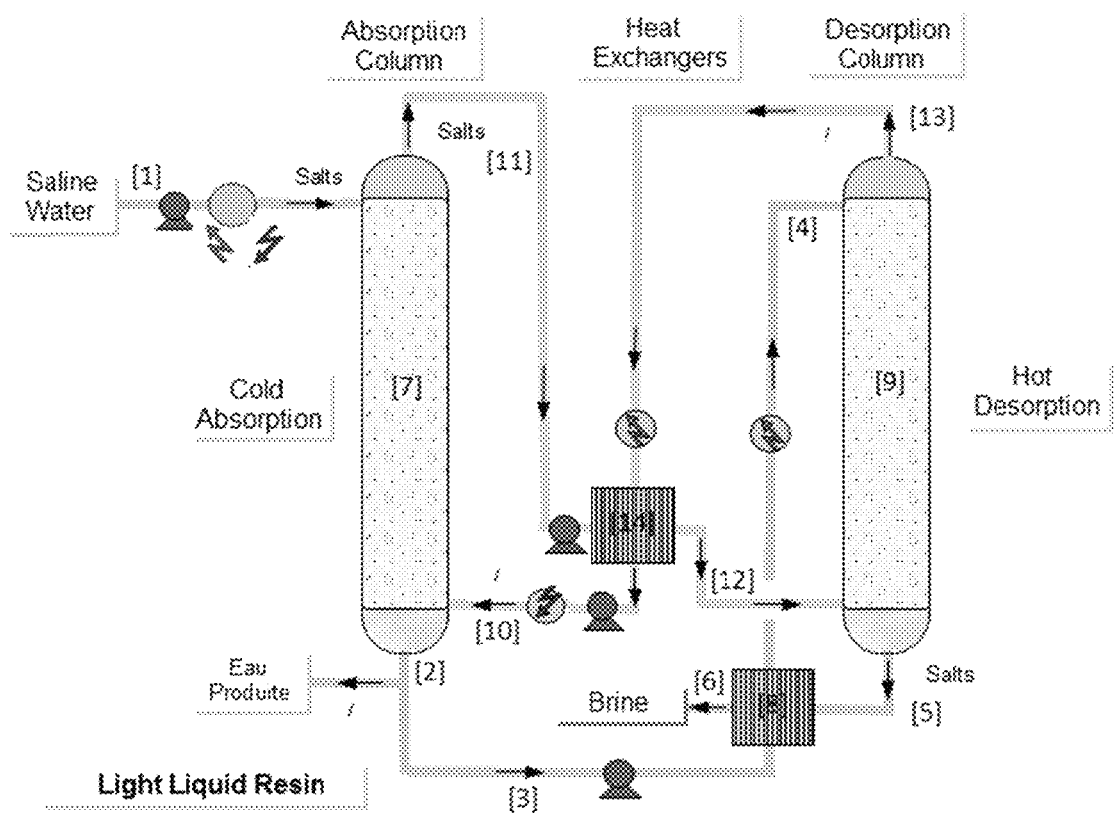
FIG. 7 is a schematic representation of another example of a device according to the invention described in Example 8.

A variant of the device and the process described in Example 7 is shown in FIG. 7. In this variant, the non water miscible organic phase is less dense than the water to be treated and the brine produced. FIG. 7 shows the same numbering used in FIG. 4. In this variant, the columns operate in reverse flows ("head down"). There is a cold section on the left of the heat exchangers and a hot section on the right of the heat exchangers (8) and (14). The elements of this device are therefore as described with reference to FIG. 4 and to example 7.

Example 9

Figure 8:
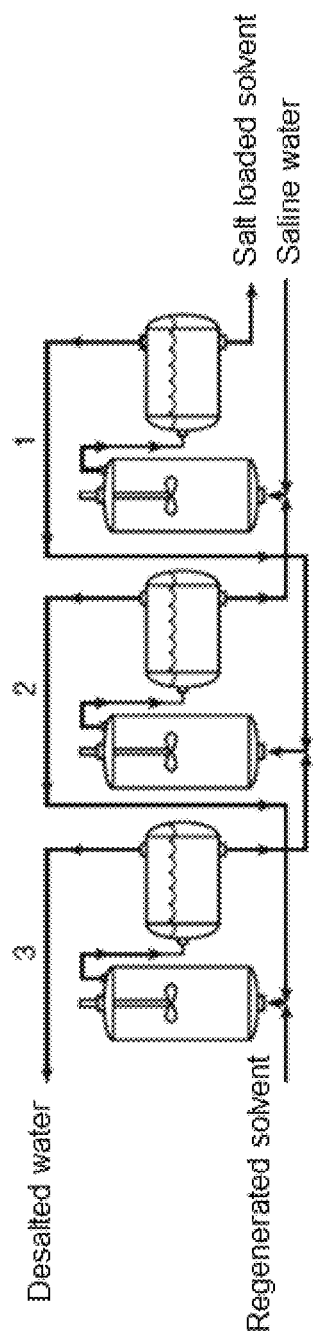
FIG. 8 is a schematic representation of another example of a device according to the invention described in Example 9.

Another variant of the device according to the invention is shown partially in FIG. 8. In this device, each of the columns (7) and (9) is replaced by the combination of a rotor/stator mixer (20) with an propeller and a settling tank (30). Each of these combinations forms an extraction/de-extraction unit, which can be connected in series in order to carry out a succession of absorption or regeneration steps. The number of steps required to desalinate seawater and obtain water where more than 99% of the sodium will have been extracted, will generally be at least 3, preferably 4 or 5 stages.

Example 10

Synthesis of Compounds ASMC7, ASMC9, ASMC11 and ASMC13

Synthesis Diagram

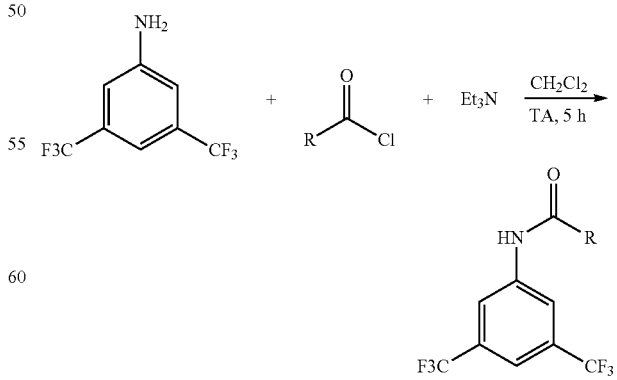

R=n-$C_7H_{15}$ (ASMC7), n-$C_9H_{19}$ (ASMC9), n-$C_{11}H_{23}$ (ASMC11), n-$C_{13}H_{27}$ (ASMC13).

Protocol

To a solution of 3.5-bis(trifluoromethyl)aniline (8.79 mL, 56.29 mmol, 1.0 eq.), dichloromethane (40 mL) and triethylamine (8.63 mL, 61.92 mmol, 1.1 eq.) is added under stirring and dropwise of acid chloride (56.29 mmol, 1.0 eq.). The temperature is controlled during the addition and must not exceed 38° C. (Boiling point of dichloromethane). The reaction mixture is stirred for 5 h at room temperature. A solution of 1M HCl (50 mL) is added and the organic phase is then washed. Successive washes are carried out with 1M HCl solution (50 mL) and saturated NaCl solution (50 mL). The organic phase is dried over $Na_2SO_4$, filtered and the solvent is then evaporated under reduced pressure. The solid residue is then taken up in petroleum ether (cold or at room temperature), washed, filtered and then dried under vacuum to give the desired amide. The petroleum ether used is a mixture of hydrocarbons composed mainly of n-pentane, 2-methyl pentane with CAS No. 64742-49-0 from VWR, where it is sold under the name Oil ether 40-60° C. GPR RECTAPUR. The compounds obtained have the following characteristics:

| R | Component | Molar weight (g/mole) | Petroleum ether T ° C. | Yield | Aspect | Melting Point |
|---|---|---|---|---|---|---|
| n-$C_7H_{15}$ | ASMC7 | 355.3 | Cold (−20° C.) | 91% | White solid | 43-44° C. |
| n-$C_9H_{19}$ | ASMC9 | 383.3 | Ambient | 92% | White solid | 79-81° C. |
| n-$C_{11}H_{23}$ | ASMC11 | 411.4 | Ambient | 92% | White solid | 60-61° C. |
| n-$C_{13}H_{27}$ | ASMC13 | 439.5 | Ambient | 90% | White solid | 53-54° C. |

Figure 9:
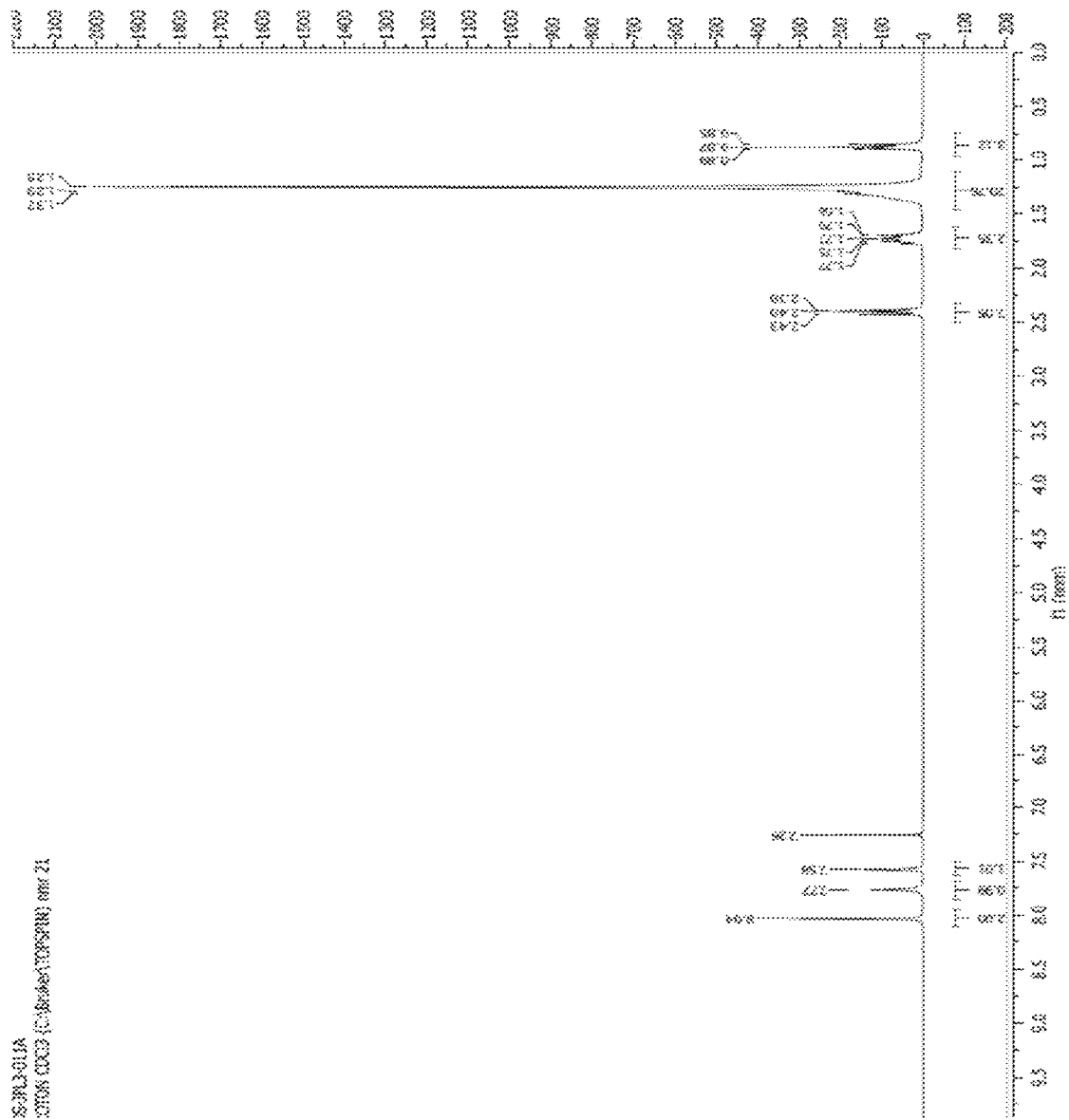
FIG. 9 shows the NMR spectrum of compound ASMC11

The compounds ASMC7, ASMC9, ASMC11 and ASMC13 have the respective IUPAC names: N-[3,5-bis(trifluoromethyl)phenyl]octanamide, N-[3,5-bis(trifluoromethyl) phenyl]decanamide, N-[3,5-bis(trifluoromethyl)phenyl]dodecanamide, N-[3,5-bis(trifluoromethyl)phenyl] tetradecanamide and were further identified by NMR spectrometry. FIG. 9 shows the NMR spectrum ($CDCl_3$, 300 MHz) of the ASMC11 compound, the peaks of which are as follows: 1 H NMR ($CDCl_3$, 300 MHz): δ (ppm)=0.87 (t, 3J=7.0 Hz, 3H), 1.20-1.35 (m, 20H), 1.73 (quint., 3J=7.0 Hz, 2H), 2.40 (t, 3J=7.0 Hz, 2H), 7.58 (s, 1H), 7.77 (bs, 1H), 8.04 (s, 2H).

Example 11

Extraction of Sodium Chloride from an Aqueous Solution by Formulations Comprising an ASM of the Amide Family and the Calix[4]Est CEM in the Presence of a Fluidifying Agent (Chloroform $CHCl_3$) and Comparison with Other ASMs and Compounds.

The ASMs of the amide family used are the compounds ASMC7, ASMC9, ASMC11, and ASMC13, the synthesis of which is described in Example 10. By way of comparison, ASM3 and 3,5-Di(trifluoromethyl)aniline (CAS No. 328-74-5) have also been used in the preparation of extracting compositions.

The extraction composition is obtained by solubilizing an amount of 4-tert-butyl Calix[4]arene tetraethyl Ester (CAS No. 97600-39-0) and ASM in chloroform $CHCl_3$ to obtain a final concentration after solubilization of the CEM and ASM of 0.3 mol/L for Calix[4]Est and of 0.3 mol/L for ASM, respectively. These sealed formulations were then orbitally stirred at 500 rpm for 2 hours after adding an equivalent volume of twice distilled water to allow water saturation of the entire formulation and control of pH output (pH=7). The extraction composition is then put to stand to settle. All the compositions tested are stable and rapidly decanted (a few minutes at the most).

A 0.4 mol/L NaCl aqueous solution was prepared from twice distilled water.

The organic extraction composition is then slightly heated to promote solubilization of the compounds by hot air gun (temperature of about 50 to 60° C.) for a few seconds (10 to 30 seconds) until a clear solution is obtained.

3 mL of the organic extraction composition is then removed from the lower phase of the settled two-phase mixture and transferred to a vial containing 3 mL of salt water at 0.4 M NaCl and then the flask is sealed and orbitally stirred (at 500 revolutions per minute), for 2 hours at room temperature (RT), that is to say between 20 and 25° C. In the case of extraction at 60° C., magnetic stirring (at 500 revolutions per minute), for 2 hours, is carried out with indirect heating in a metal mold on a heating plate. It is verified that droplets of the order of 1-2 mm are present during these agitations in order to be certain to achieve equilibrium in the NaCl distribution between the two liquid phases at the end of stirring. The appearance of the organic and aqueous phases is clear and colorless or slightly cloudy.

After stirring for 2 hours, stirring is stopped and the solution is put to stand to settle within 10 minutes, at least until the two phases have completely separated off, at the temperature of the test. The upper aqueous phase is then removed and then stirred and diluted for analysis of its salinity by a Metrohm Ion Chromatograph incorporating a suitable cation analysis column and a suitable anion analysis column. Similarly, the initial aqueous solution of NaCl at 0.4M is also analyzed by this ion chromatograph to determine its relative molar concentration in sodium and in chlorides. All extractions and analyzes were duplicated. The table below shows the results observed for an iso-molar distribution of ASM and CEM:

| ASM tested | Concentration of CEM in Mol/L | Concentration of ASM in Mol/L | Appearance after saturation with water | Extraction T (° C.) | Mol % Na+ extracted from the water to be treated | Mol % Cl− extracted from the water to be treated |
|---|---|---|---|---|---|---|
| ASMC13 | 0.300 | 0.300 | Slightly cloudy | RT | 22.7% | 26.2% |
| ASMC13 | 0.300 | 0.300 | Slightly cloudy | RT | 23.8% | 27.4% |
| ASMC13 | 0.300 | 0.300 | Slightly cloudy | 60° C. | 5.9% | 6.9% |
| ASMC13 | 0.300 | 0.300 | Slightly cloudy | 60° C. | 9.0% | 9.4% |
| ASMC11 | 0.300 | 0.300 | Slightly cloudy, Some crystals | RT | 22.4% | 24.5% |
| ASMC11 | 0.300 | 0.300 | Slightly cloudy, Some crystals | RT | 23.1% | 25.3% |
| ASMC11 | 0.300 | 0.300 | Slightly cloudy, Some crystals | 60° C. | 3.4% | 4.9% |

|  | Concentration of CEM in Mol/L | Concentration of ASM in Mol/L | Appearance after saturation with water | Extraction T (° C.) | Mol % Na+ extracted from the water to be treated | Mol % Cl- extracted from the water to be treated |
| --- | --- | --- | --- | --- | --- | --- |
| ASM tested | | | | | | |
| ASMC11 | 0.300 | 0.300 | Slightly cloudy, Some crystals | 60° C. | 7.1% | 7.7% |
| ASMC9 | 0.300 | 0.300 | Slightly cloudy | RT | 25.2% | 27.1% |
| ASMC9 | 0.300 | 0.300 | Slightly cloudy | RT | 21.7% | 23.8% |
| ASMC9 | 0.300 | 0.300 | Slightly cloudy | 60° C. | 5.4% | 6.9% |
| ASMC9 | 0.300 | 0.300 | Slightly cloudy | 60° C. | 5.7% | 8.0% |
| ASMC7 | 0.304 | 0.304 | Clear | RT | 23.6% | 26.3% |
| ASMC7 | 0.304 | 0.304 | Clear | RT | 22.8% | 25.9% |
| ASMC7 | 0.304 | 0.304 | Clear | 60° C. | 5.5% | 7.6% |
| ASMC7 | 0.304 | 0.304 | Clear | 60° C. | 5.4% | 7.3% |
| ASM3 | 0.300 | 0.300 | Clear | RT | 6.8% | 8.2% |
| ASM3 | 0.300 | 0.300 | Clear | RT | 7.6% | 8.8% |
| ASM3 | 0.300 | 0.300 | Clear | 60° C. | not detected | not detected |
| ASM3 | 0.300 | 0.300 | Clear | 60° C. | not detected | not detected |
| AnilineF* | 0.300 | 0.295 | Clear | RT | 2.0% | 4.3% |
| AnilineF* | 0.300 | 0.295 | Clear | RT | 1.8% | 2.9% |
| AnilineF* | 0.300 | 0.295 | Clear | 60° C. | not detected | not detected |
| AnilineF* | 0.300 | 0.295 | Clear | 60° C. | not detected | not detected |

* 3,5-Di(trifluoromethyl)aniline

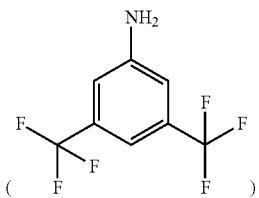 [SMILES: Nc1cc(C(F)(F)F)cc(C(F)(F)F)c1]

The average results for the molar extraction of sodium chloride can therefore be summarized in the following table:

|  | Salt, T | | |
| --- | --- | --- | --- |
| ASM | NaCl - 20° C. % ext | NaCl - 60° C. % ext | Δ % ext |
| ASMC7 | 24.6% | 6.3% | 18.4% |
| ASMC9 | 24.4% | 6.5% | 17.9% |
| ASMC11 | 23.8% | 5.8% | 18.0% |
| ASMC13 | 25.0% | 7.8% | 17.2% |
| ASM3 | 7.9% | 0.0% | 7.9% |
| AnilineF* | 2.7% | 0.0% | 2.7% |

It therefore appears on the one hand that the anionic solvating agents of the amide family (ASMC7-13) according to the invention are more active than the anionic solvating agents of the alcohols family (ASM3). In particular, they allow an efficient capture at ambient temperature and a sufficient release of the ionic species at a higher temperature but sufficiently low (especially below 150° C.). It also appears that the amine version AnilineF* is even less active than alcohol with identical concentration. However, these compounds can be used in extraction compositions according to the invention simply by increasing its ASM concentration above 2 mol/L (see examples 6).

This overactivity of the amides is also maintained when the alkyl chain of the amide function is extended from $C_7H_{15}$ to $C_{13}H_{27}$, which makes it possible to ensure good water non solubility of this family of anionic solvating agents.

Example 12

Extraction of Sodium Chloride from an Aqueous Solution by Formulations Comprising the ASMC7 from the Amide Family at Four Different Concentrations and the CEM Calix[4]Est at Constant Concentration in the Presence of a Fluidifying Agent ($CHCl_3$) and Comparison of the Associated Extraction Performance Four extraction compositions were obtained by solubilizing a constant amount of 4-tert-butylCalix[4]arene tetraethylEster (CAS No. 97600-39-0) and four increasing amounts of ASMC7 in chloroform $CHCl_3$ to obtain four final concentrations after solubilization of CEM and ASM, from 0.34 to 0.36 mol/L for Calix[4]Est and 0.36 mol/L, 0.71 mol/L, 1.09 mol/L and 1.49 mol/L for ASMC7, respectively. These four sealed formulations were then orbitally stirred at 500 rpm for 2 hours after adding an equivalent volume of twice distilled water to allow water saturation of the entire formulation and control of pH at the output (pH=7). The extraction composition is then put to stand for settling. All the compositions tested are stable and rapidly decanted (a few minutes at the most).

An 0.3 mol/L NaCl aqueous solution was prepared from twice distilled water.

3 ml of each organic extraction composition are then removed in the lower phase of the settled two-phase mixture and transferred to four vials, each containing 3 ml of the salt water at 0.3M NaCl, then the flasks are sealed and orbitally stirred (at 500 revolutions per minute), for 2 hours at room temperature (RT), that is to say between 20 and 25° C. In the case of extraction at 60° C., a magnetic stirring (at 500 revolutions per minute), for 2 hours, is carried out with indirect heating in a metal mold on a heating plate. It is verified that droplets of the order of 1-2 mm are present during these agitations in order to be certain to reach equilibrium in the NaCl distribution between the two liquid phases at the end of stirring. The appearance of the organic and aqueous phases is clear and colorless for these 4 formulations tested.

After stirring for 2 hours, stirring is stopped and the solution is put to stand for settling within 10 minutes, at least until the two phases have completely separated off, at the test temperature. Then, the four upper aqueous phases are separately taken and then stirred and diluted for analysis of their salinity by a Metrohm Ion Chromatograph incorporating a suitable cation analysis column and a suitable anion analysis column. Similarly, the initial aqueous solution of 0.3M NaCl is also analyzed by this ion chromatograph to determine its relative molar concentration of sodium and chlorides. All extractions and analyzes were duplicated. The below table shows the results observed for four molar distributions between ASM and CEM:

| Concentration of CEM in Mol/L | Concentration of ASMC7 in Mol/L | Concentration ratios [ASMC7]/[ASM] | Aspect after water saturation | Extraction T (° C.) | Mol % of Na+ extracted from water to be treated | Mol % of Cl− extracted from water to be treated |
|---|---|---|---|---|---|---|
| 0.345 | 0.358 | 1.04 | Clear | RT | 27.9% | 27.9% |
| 0.345 | 0.358 | 1.04 | Clear | RT | 21.7% | 27.2% |
| 0.345 | 0.358 | 1.04 | Clear | 60° C. | 9.9% | 13.0% |
| 0.345 | 0.358 | 1.04 | Clear | 60° C. | 13.1% | 14.1% |
| 0.341 | 0.708 | 2.08 | Clear | RT | 44.2% | 44.4% |
| 0.341 | 0.708 | 2.08 | Clear | RT | 45.1% | 44.4% |
| 0.341 | 0.708 | 2.08 | Clear | 60° C. | 28.1% | 26.6% |
| 0.341 | 0.708 | 2.08 | Clear | 60° C. | 28.2% | 27.4% |
| 0.349 | 1.088 | 3.12 | Clear | RT | 60.0% | 51.2% |
| 0.349 | 1.088 | 3.12 | Clear | RT | 59.8% | 52.9% |
| 0.349 | 1.088 | 3.12 | Clear | 60° C. | 37.7% | 31.0% |
| 0.349 | 1.088 | 3.12 | Clear | 60° C. | 39.5% | 30.4% |
| 0.358 | 1.488 | 4.16 | Clear | RT | 71.2% | 64.6% |
| 0.358 | 1.488 | 4.16 | Clear | RT | 65.0% | 65.6% |
| 0.358 | 1.488 | 4.16 | Clear | 60° C. | 48.4% | 45.6% |
| 0.358 | 1.488 | 4.16 | Clear | 60° C. | 46.9% | 39.9% |

The average results for the extraction of sodium chloride can thus be summarized in the following table:

| | Salt, T | | |
|---|---|---|---|
| [ASMC7]/[CEM] | NaCl - 20° C. % ext | NaCl - 60° C. % ext | Δ % ext |
| 1.04 | 26.2% | 12.5% | 13.6% |
| 2.08 | 44.5% | 27.6% | 16.9% |
| 3.12 | 55.9% | 34.5% | 21.3% |
| 4.16 | 66.6% | 45.1% | 21.4% |

It appears a regular and almost linear rise of the NaCl extraction rate with an increase of the relative concentration of ASMC7, at ambient temperature or at 60° C., showing the importance of poly-solvatation of the Chloride anion ASM to allow a good NaCl extraction. It should also be noted that not all CEMs are used for 0.3 M NaCl initial salinity, leaving room for extra extraction for higher salinity.

The invention is not limited to the embodiments presented and other embodiments will become apparent to those skilled in the art. In particular, it is possible to use this method to upgrade water from many sources of natural or industrial salt water. It is also possible to employ this method in order to allow salt reconcentration by increasing the regeneration temperature or to selectively extract certain salts having, for example, a certain economic value or promoting scale formation. In addition, with certain improvements, this method will be able to treat produced water or industrial water for the production of process water, in order to limit environmental impacts associated with salt water discharges into natural environments.

The invention may also incorporate embodiments where several ECMs will be dissolved in an ASM, a mixture of ASMs or an ASM and a fluidifying agent or a mixture of ASMs and fluidifying agents in order to allow the extraction of a larger panel of Cations and anions; their associated counter-ions.

The invention claimed is:

1. A method for treating water comprising the extraction of at least two ionic species, the at least two ionic species comprising an anionic species and a cationic species and being present in the water to be treated, the method comprising the following steps:

a) mixing in a first reactor, at a first temperature, a hydrophobic organic liquid phase and the water to be treated, the water to be treated being in the liquid state, in order to subsequently obtain a treated liquid water and a hydrophobic organic liquid phase charged with the at least two ionic species, the hydrophobic organic liquid phase comprising:

at least a first protic and hydrophobic organic compound allowing anionic species solvation and whose pKa in water at 25° C. is at least 9 and at least lower than 15 at 25° C., the first protic and hydrophobic organic compound being a compound of Formula (B):

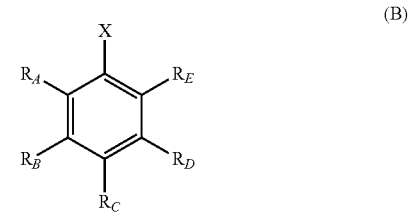

in which at least one of the radicals $R_A$, $R_B$, $R_C$, $R_D$ and $R_E$, which are identical or different, is a halogen atom or an electron-withdrawing group or a halogenated radical, of the following group: F, Cl, Br, $C_mF_{2m+1}$ with m≤4, where m is a non-zero integer; $CF_2CF_2C_pH_{2p+1}$ with p≤4, where p is an integer; $CF_2C_pH_{2p+1}$ with p≤4, where p is an integer; $CH_2C_pF_{2p+1}$ with p≤4, where p is an integer; $OCH_2CF_3$; $C(=O)CF_3$; $C_mH_nF_pCl_qBr_s$ with m≤4, where n, p, q, s are integers of which at least p, q or s is non-zero; $C(=O)OC_mH_{2m+1}$ with m≤4, where m is an integer; and $C(=O)C_mH_{2m+1}$ with m≤4, where m is an integer, the remaining radical(s) $R_A$, $R_B$, $R_C$, $R_D$ and $R_E$ are chosen, identical or different, from the following non-electron withdrawing radicals: H; $CH_3$; $CH_2CH_3$; $CH_2CH_2C_pF_{2p+1}$ with p≤4, where p is an integer; $C_mH_{2m-1}$ with m≤10, where m is a non-zero integer; and $C_mH_{2m+1}$ with m≤10, where m is a non-zero integer;

where only one of the radicals $R_A$ to $R_E$ may be one of these last two radicals $C_mH_{2m-1}$ and $C_mH_{2m+1}$; and wherein X is selected from the following radicals: OH; NH—R';

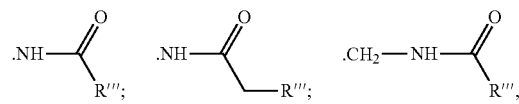

where R' and R", is chosen from the following radicals: H; $C_nH_{2n-1}$ with n≤4, where n is a non-zero integer; $C_nH_{2n+1}$ with n≤4, where n is a non-zero integer; $CH_2CH_2C_pF_{2p+1}$ with p≤4, where p is an integer; $CH_2C_pF_{2p+1}$ with p≤4, where p is an integer; $CF_2C_pH_{2p+1}$ with p≤4, where p is an integer; $CF_2CF_2C_pH_{2p+1}$ with p≤4, where p is an integer; $C_mF_{2m+1}$ with m≤4, where m is a non-zero integer; $C_mH_nF_pCl_qBr_s$ with m≤4, where n, p, q, s are integers of which at least p, q or s is non-zero; and an aryl radical of formula (b):

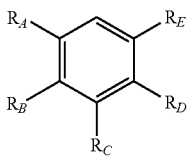

where $R_A$, $R_B$, $R_C$, $R_D$ and $R_E$, which may be identical or different, are as defined above in formula (B);

and wherein R''' is selected from the following radicals: $C_mH_{2m+1}$ with m≤20, where m is an integer; $C_mH_{2m-1}$ with m≤20, where m is a non-zero integer; $C_mH_nF_pCl_qBr_s$ with m≤10, where n, p, q, s are integers of which at least p, q or s is non-zero; $CH_2C_{H2}C_pF_{2p+1}$ with p≤4, where p is an integer; $CH_2C_pF_{2p+1}$ with p≤4, where p is an integer; $CF_2C_pH_{2p+1}$ with p≤4, where p is an integer; $CF_2CF_2C_pH_{2p+1}$ with p≤4, where p is an integer; $C_mF_{2m+1}$ with m≤4, where m is a non-zero integer; and an aryl radical of formula (b):

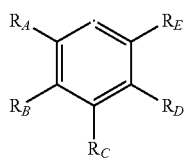

where $R_A$, $R_B$, $R_C$, $R_D$ and $R_E$, which may be identical or different, are as defined above in formula (B); and at least a second hydrophobic organic compound allowing cation extraction and having a complexing constant of the cationic species whose log K value, in methanol at 25° C., is greater than 2 and less than 11;

b) separating of the treated liquid water and of the organic liquid phase charged with the at least two ionic species, c) mixing, at a second temperature, in the liquid phase, in a second reactor, of the organic liquid phase, charged with the at least two ionic species, with regeneration liquid water, for subsequent production of a regenerated organic liquid phase and of a regeneration liquid water charged with the at least two ionic species, the second temperature being higher than the first temperature and the difference between the first and second temperatures ranging from 30° C. to 150° C.

2. The method according to claim 1, wherein the method does not comprise a step in which the pH of the regeneration liquid water is significantly modified.

3. The method according to claim 1, wherein the method comprises the following steps:

d) separating the regenerated organic liquid phase and regeneration liquid water charged with the at least two ionic species, e) indirect thermal contacting of the organic liquid phase charged with the at least two ionic species and the regenerated organic liquid phase.

4. The method according to claim 1, wherein the method comprises a step of heating the regeneration liquid water carried out before step c).

5. The method according to claim 1, wherein the anionic species is chloride or sulphate, or nitrate.

6. The method according to claim 1, wherein the first protic and hydrophobic organic compound allowing anionic species solvation has a pKa in water at 25° C. of at least 10.5 and lower than the pKa of water at 25° C.

7. The method according to claim 1, wherein the second hydrophobic compound allowing cation extraction has a complexing constant of the cationic species whose log K value in methanol at 25° C. is greater than 3 and less than 9.

8. The method according to claim 1, wherein compound (B) is a compound in which X represents:

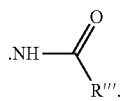

9. The method according to claim 8, wherein compound (B) is represented by formula:

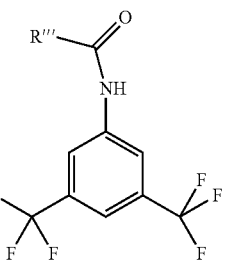

or

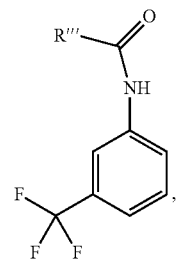

in which R'''' is chosen from the following radicals: $C_mH_{2m+1}$ with m <20, where m is an integer; $C_mH_{2m-1}$ with m≤20, where m is a non-zero integer; $C_mH_nF_pCl_qBr_s$ with m≤10, where n, p, q, s are integers of which at least p, q or s is non-zero; and an aryl radical of formula (b):

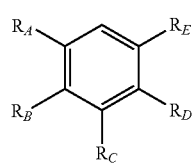

in which at least one of the radicals $R_A$, $R_B$, $R_C$, $R_D$ and $R_E$, which are identical or different, is a halogen atom or an electron-withdrawing group or a halogenated radical, of the following group: F, Cl, Br, $C_mF_{2m+1}$ with m≤4, where m is a non-zero integer; $CF_2CF_2C_pH_{2p+1}$ with p≤4, where p is an integer; $CF_2C_pH_{2p+1}$ with p≤4, where p is an integer; $CH_2C_pF_{2p+1}$ with p≤4, where p is an integer, $OCH_2CF_3$; $C(=O)CF_3$; $C_mH_nF_pCl_qBr_s$ with m≤4, where n, p, q, s are integers of which at least p, q or s is non-zero; C(=O)OC$_m$H$_{2m+1}$ with m≤4, where m is an integer; and C(=O)C$_m$H$_{2m+1}$ with m≤4, where m is an integer, the remaining radical(s) R$_A$, R$_B$, R$_C$, R$_D$ and R$_E$ are chosen, identical or different, from the following non-electron withdrawing radicals: H; CH$_3$; CH$_2$CH$_3$; CH$_2$CH$_2$C$_p$F$_{2p+1}$ with p≤4, where p is an integer; C$_m$H$_{2m-1}$ with m≤10, where m is a non-zero integer; and C$_m$H$_{2m+1}$ with m≤10, where m is a non-zero integer, where only one of the radicals R$_A$ to R$_E$ may be one of these last two radicals C$_m$H$_{2m-1}$ and C$_m$H$_{2m+1}$.

10. The method according to claim 9, wherein radical the R''' radical is n-C$_7$H$_{15}$, n-C$_9$H$_{19}$, n-C$_{11}$H$_{23}$ or n-C$_{13}$H$_{27}$.

11. The method according to claim 10, wherein compound (B) is chosen among: N-[3,5-bis(trifluoromethyl)phenyl] octanamide; N-[3,5-bis(trifluoromethyl)phenyl] decanamide; N-[3,5-bis(trifluoromethyl)phenyl] dodecanamide; and N-[3,5-bis(trifluoromethyl)phenyl] tetradecanamide.

12. The method according to claim 1, wherein compound (B) is represented by formula:

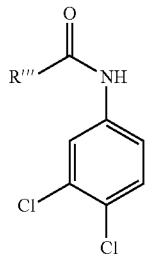

in which R''' is chosen from the following radicals: C$_m$H$_{2m+1}$ with m≤20, where m is an integer; C$_m$H$_{2m-1}$ with m≤20, where m is a non-zero integer; C$_m$H$_n$F$_p$Cl$_q$Br$_s$ with m≤10, where n, p, q, s are integers of which at least p, q or s is non-zero; and an aryl radical of formula (b):

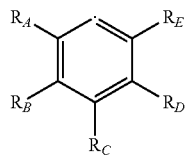

(b)

in which at least one of the radicals R$_A$, R$_B$, R$_C$, R$_D$ and R$_E$, which are identical or different, is a halogen atom or an electron-withdrawing group, in particular a halogenated radical, of the following group: F, Cl, Br, C$_m$F$_{2m+1}$ with m≤4, where m is a non-zero integer; CF$_2$CF$_2$C$_p$H$_{2p+1}$ with p≤4, where p is an integer; CF$_2$C$_p$H$_{2p+1}$ with p≤4, where p is an integer: CH$_2$C$_p$F$_{2p+1}$ with p≤4, where p is an integer; OCH$_2$CF$_3$; C(=O)CF$_3$; C$_m$H$_n$F$_p$Cl$_q$Br$_s$ with m≤4, where n, p, q, s are integers of which at least p, q or s is non-zero; C(=O)OC$_m$H$_{2m+1}$ with m≤4, where m is an integer; and C(=O)C$_m$H$_{2m+1}$ with m≤4, where m is an integer, the remaining radical(s) R$_A$, R$_B$, R$_C$, R$_D$ and R$_E$ are chosen, identical or different, from the following non-electron withdrawing radicals: H; CH$_3$; CH$_2$CH$_3$; CH$_2$CH$_2$C$_p$F$_{2p+1}$ with p≤4, where p is an integer; C$_m$H$_{2m-1}$ with m≤10, where m is a non-zero integer; and C$_m$H$_{2m+1}$ with m≤10, where m is a non-zero integer; where only one of the radicals R$_A$ to R$_E$ may be one of these last two radicals C$_m$H$_{2m-1}$ and C$_m$H$_{2m+1}$.

13. The method according to claim 1, wherein the second hydrophobic organic compound is a crown ether having from 14 to 80 carbon atoms.

14. The method according to claim 13, wherein the second hydrophobic organic compound is selected from 6,7,9,10,12,13,20,21,23,24-decahydrodibenzo[b,k][1,4,7,10,12,16,19] heptaoxa-cyclohenicosine (DB21C7), benzo[b]-1,4,7,10,13-pentaoxacyclopentadecane (B15C5), perhydrobenzo[b]-1,4,7,10,13-pentaoxacyclopentadecane (015C5), dicyclohexano-1,4,7,10,13,16-hexaoxacyclooctadecane (DC18C6), dibenzo[b,k]-1,4,7,10,13,16-hexaoxacyclooctadecane (DB18C6) and 6,7,9,10,12,13,20,21,23,24,26,27-dodécahydrodibenzo[b,n] [1,4,7,10,13,16,19,22] octaoxacyclotetracosine (DB24C8).

15. The method according to claim 13, wherein the second hydrophobic organic compound is a substituted calixarene comprising from 32 to 80 carbon atoms.

16. The method according to claim 15, wherein the second hydrophobic organic compound is 4-tert-butylcalix[4]-arene-O,O',O'',O'''-tetraacetic acid tetraethyl ester.

* * * * *